United States Patent
Leung

(10) Patent No.: US 10,613,099 B2
(45) Date of Patent: Apr. 7, 2020

(54) CELL LINES EXPRESSING SURFACE BOUND ANTI-IDIOTYPE ANTIBODIES AGAINST ANTI-CD22 ANTIBODIES AND USES THEREOF

(71) Applicant: SINOMAB BIOSCIENCE LIMITED, Shatin (CN)

(72) Inventor: Shui-on Leung, Fanling (CN)

(73) Assignee: Sinomab Bioscience Limited, Shatin, NT (HK)

( * ) Notice: Subject to any disclaimer, the term of this patent is extended or adjusted under 35 U.S.C. 154(b) by 4 days.

(21) Appl. No.: 15/186,999

(22) Filed: Jun. 20, 2016

(65) Prior Publication Data

US 2016/0363597 A1    Dec. 15, 2016

Related U.S. Application Data

(62) Division of application No. 14/407,988, filed as application No. PCT/US2013/046053 on Jun. 16, 2013, now Pat. No. 9,371,396.

(60) Provisional application No. 61/660,327, filed on Jun. 15, 2012.

(51) Int. Cl.
| | |
|---|---|
| C12P 21/06 | (2006.01) |
| C12P 21/04 | (2006.01) |
| G01N 33/68 | (2006.01) |
| A61K 39/395 | (2006.01) |
| C07K 16/28 | (2006.01) |
| C07K 16/42 | (2006.01) |
| C07K 16/00 | (2006.01) |
| A61K 39/44 | (2006.01) |

(52) U.S. Cl.
CPC ..... *G01N 33/686* (2013.01); *A61K 39/39566* (2013.01); *C07K 16/2803* (2013.01); *C07K 16/4258* (2013.01); *A61K 39/44* (2013.01); *C07K 2317/20* (2013.01); *C07K 2317/33* (2013.01); *C07K 2317/565* (2013.01); *C07K 2317/622* (2013.01); *C07K 2317/64* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| | | |
|---|---|---|
| 5,928,904 A | 7/1999 | Holmes et al. |
| 7,321,026 B2 | 1/2008 | Leung |
| 2009/0148449 A1 | 6/2009 | DeWeers et al. |

FOREIGN PATENT DOCUMENTS

| | | |
|---|---|---|
| WO | WO 2001/75067 A2 | 10/2001 |
| WO | WO 2012/030982 A1 | 3/2012 |

OTHER PUBLICATIONS

Janeway et al., Immunology Third Edition, Garland Publishing Inc. Chapter 3, Structure of the Antibody Molecule and Immunoglobulin Genes, pp. 3:1-3:11. (Year: 1997).*
Rudikoff et al., PNAS. vol. 79 p. 1979-83 (Year: 1982).*
Zhao, Qi et al., "Generation of Anti-Idiotypic scFV for Pharmacokinetic Measurement in Lymphoma Patients Treated with Chimera Anti-CD22 Antibody SM03", *PLOS ONE*, vol. 9, No. 5 May 2014.
Extended European Search Report for Application No. EP 13.804606.5 (European National Phar of PCT/US2013/046053) dated May 3, 2016.
De Pascalis et al., "Grafting of Abbreviated Complementarity Determining Regions Containing Specificity Determining Residues Essential for Ligand Contact to Engineer a Less Immunogenic Humanized Monoclonal Antibody", *Journal of Immunology*, vol. 169, pp. 3076-3084, 2002.
Dorner, T et al., "Initial Clinical Trial of Epratuzumab (Humanized Anti-CD22 Antibody) for Immunotherapy of Systemic Lupus Erythematosus", *Arthritis Research and Therapy*, vol. 8, No. R74, pp. 1-11, Apr. 21, 2006.
Li, S. et al., "Pharmacokinetics and Tolerability of Human Mouse Chimeric Anti-CD22 Monoclonal Antibody in Chinese Patients with CD22-positive Non-Hodgkin Lymphoma", *mAbs*, vol. 4, No. 2, pp. 256-266, Mar. 1, 2012.

(Continued)

*Primary Examiner* — Chun W Dahle
(74) *Attorney, Agent, or Firm* — Chalin A. Smith; Smith Patent, LLC

(57) ABSTRACT

The present invention describes the generation of an anti-idiotype single-chain Fv (scFv) antibody specific for the murine (RFB4), chimeric (SM03) and humanized (SM06) versions of an anti-CD22 antibody ("the anti-CD22 antibodies"). The present invention further describes the construction of a murine IgG2a/kappa immunoglobulin carrying the variable region sequences of the anti-idiotype scFv sequences. Additionally, the present invention provides a cell line capable of producing an anti-idiotype murine antibody specific for "the anti-CD22 antibodies." The present invention is directed against a method for identifying and evaluating the activities and concentration of "the anti-CD22 antibodies." Additionally, the present invention provides a method for evaluating serum concentration of "the anti-CD22 antibodies" that are being used clinically. The present invention is also directed against a method to detect HAMA, HACA and HAHA responses in patients treated with "the anti-CD22 antibodies." Specifically, the present invention is directed against the establishment of a cell line expressing surface concentration of the antibody of the invention; the said cell line expressing surface anti-idiotype antibodies or antibody fragments will be used as the target cell line for evaluating the functional activities of "the anti-CD22 antibodies" via complement dependent cytotoxicity (CDC) and/or antibody dependent cell cytotoxicity (ADCC) activities.

14 Claims, 20 Drawing Sheets
Specification includes a Sequence Listing.

(56) References Cited

OTHER PUBLICATIONS

Losman, M. et al., "Development and Evaluation of the Specificity of a Rat Monoclonal Anti-Idiotype Antibody, WN, to an Anti-B-Cell Lymphoma Monoclonal Antibody, LL2", *Cancer Research*, vol. 55, p. 5978s-5982s, Dec. 1, 1995.

Maccallum et al., "Antibody-antigen interactions: contact analysis and binding site topography", *Journal of Molecular Biology*, vol. 262, pp. 732-745, 1996.

Messmann et al., "A Phase I Study of Combination Therapy with Immunotoxins IgG-HD37-Deglycosylated Ricin A Chain (dgA) and IgG-RFB4-dgA (Combotox) in Patients with Refractory CD19(+), CD22(+) B Cell Lymphoma", *Clinical Cancer Research*, vol. 6, 1302-1313, Apr. 2000.

D. Campana, et al., "Human B cell Development. I. Phenotypic Differences of B Lymphocytes in the Bone Marrow and Peripheral Lymphoid Tissue", *Journal of Immunology*, vol. 134, pp. 1524-1530 (1985). (Abstract Only).

Shui-on Leung, et al., "Surrogate Target Cells Expressing Surface Anti-Idiotype Antibody for the Clinical Evaluation of an Internalizing CD-22-specific Antibody", *Monoclonal Antibodies*, vol. 7, No. 1, pp. 66-76 (2015).

Jia-Ling Li, et al., "The Epitope Specificity and Tissue Reactivity of Four Murine Monoclonal Anti-CD22 Antibodies", *Cellular Immunology*, vol. 118, pp. 85-99 (1989).

Su Li, et al. "Pharmacokinetics and Tolerability of Human Mouse Chimeric Anti-CD22 Monoclonal Antibody in Chinese Patients With CD22-Positive Non-Hodgkin's Lymphoma", *Landes Bioscience Journal*, vol. 4, No. 2, pp. 256-266 (2012).

Rui-an Liang, et al. "Framework-reengineering and its Application in Humanized Antibody fSM03", *Chinese J New Drugs*, vol. 15, No. 21. pp. 1832-1836 (2006). (Abstract Only).

\* cited by examiner

Figure 2

Fig. 2A. Heavy Chain CDR Sequences -

CDR1: NYVTH (SEQ ID NO: 1)

CDR2: YINPYSDGSKYNEKFKG (SEQ ID NO: 2)

CDR3: GKTEWFPY (SEQ ID NO: 3)

Fig 2B. Light Chain CDR Sequences -

CDR1: KASQSVDYDGDSYMN (SEQ ID NO: 4)

CDR2: AASNLES (SEQ ID NO: 4)

CDR3-1: QQSNKDP<u>F</u>T (SEQ ID NO: 6)

CDR3-2: QQSNKDP<u>Y</u>T (SEQ ID NO: 6)

Figure 3

QVQLVQSGPELVKPGASVKMSCKASGYTFT NYVTH WVKQKPGQGLEWIG YINPYSDGSKYNEKFKG

KATLTSDESSSTAYMEVSSLTSEDSAVYYCAR GKTEWFPY WGQGTPLTVS GGGGSGGGGSGGGGSGGGGDIVL

TQTPASLAVSLGQRATISC KASQSVDYDGDSYMN WYQQKPGQPPKLLIY AASNLES GIPARFSGS

GSGTDFTLNIHPVEEEDAATYYC QQSNEDPFT FGGGTKLEI (SEQ ID NO: 7)

Figure 7

Fig. 7A: Heavy chain immunoglobulin DNA Sequence: (SEQ ID NO: 8)

CAGGTCCAACTGCAGCAGTCTGGACCTGAGCTGGTAAAGCCTGGGGCTTCAGTGAAGATGTCCTGCAAGGCTTCTGGAT
ACACATTCACTAACTATGTTACGCACTGGGTGAAGCAGAAGCCTGGGCAGGGCCTTGAGTGGATTGGATATATTAATCCT
TACAGTGATGGTTCTAAGTACAATGAGAAGTTCAAAGGCAAGGCCACACTGACTTCAGACGAATCCTCCAGCACAGCCTA
CATGGAGCTCAGCAGCCTGACCTCTGAGGACTCTGCGGTCTATTACTGTGCAAGAGGGAAAACCGAGTGGTTTCCTTACT
GGGGTCAAGGCACTACGGTCACCGTCTCCTCAGCCAAAACAACAGCCCCATCGGTCTATCCACTGGCCCCTGTGTGTGGAGAT
ACAACTGGCTCTTCGGTGACTCTAGGATGCCTGGTCAAGGGTTATTTCCCTGAGCCAGTGACCTTGACCTGGAACTCTGGATCCC
TGTCCAGTGGTGTGCACACCTTCCCAGCTGTCCTGCAGTCTGACCTCTACACCCTCAGCAGCTCAGTGACTGTAACCTCGAGCACC
TGGCCCAGCCAGTCCATCACCTGCAATGTGGCCCACCCGGCAAGCAGCACCAAGGTGGACAAGAAAATTGAGCCCAGAGGGCCC
ACAATCAAGCCCTGTCCTCCATGCAAATGCCCAGCACCTAACCTCTTGGGTGGACCATCCGTCTTCATCTTCCCTCCAAAGATCAA
GGATGTACTCATGATCTCCCTGAGCCCCATAGTCACATGTGTGGTGGTGGATGTGAGCGAGGATGACCCAGATGTCCAGATCAGC
TGGTTTGTGAACAACGTGGAAGTACACACAGCTCAGACACAAACCCATAGAGAGGATTACAACAGTACTCTCCGGGTGGTCAGT
GCCCTCCCCATCCAGCACCAGGACTGGATGAGTGGCAAGGAGTTCAAATGCAAGGTCAACAACAAAGACCTCCCAGCGCCCATC
GAGAGAACCATCTCAAAACCCAAAGGGTCAGTAAGAGCTCCACAGGTATATGTCTTGCCTCCACCAGAAGAAGAGATGACTAAG
AAACAGGTCACTCTGACCTGCATGGTCACAGACTTCATGCCTGAAGACATTTACGTGGAGTGGACCAACAACGGGAAAACAGAG
CTAAACTACAAGAACACTGAACCAGTCCTGGACTCTGATGGTTCTTACTTCATGTACAGCAAGCTGAGAGTGGAAAAGAAGAAC
TGGGTGGAAAGAAATAGCTACTCCTGTTCAGTGGTCCACGAGGGTCTGCACAATCACCTTACGACTAAGACCATCTCCCGGTCTC
TGGGTAAATAA

Figure 7 (Continued)

Fig. 7B: Heavy Chain Translated Sequence: (SEQ ID NO: 9)

QVQLQQSGPELVKPGASVKMSCKASGYTFTNYVTHWVKQKPGQGLEWIGYINPYSDGSKYNEKFKGKATL
TSDESSSTAYMELSSLTSEDSAVYYCARGKTEWFPYWGQGTTVTVSSAKTTAPSVYPLAPVCGDTTGSSVTLG
CLVKGYFPEPVTLTWNSGSLSSGVHTFPAVLQSDLYTLSSSVTVTSSTWPSQSITCNVAHPASSTKVDKKIEPRGPTI
KPCPPCKCPAPNLLGGPSVFIFPPKIKDVLMISLSPIVTCVVVDVSEDDPDVQISWFVNNVEVHTAQTQTHREDYNS
TLRVVSALPIQHQDWMSGKEFKCKVNNKDLPAPIERTISKPKGSVRAPQVYVLPPPEEEMTKKQVTLTCMVTDFM
PEDIYVEWTNNGKTELNYKNTEPVLDSDGSYFMYSKLRVEKKNWVERNSYSCSVVHEGLHNHLTTKTISRSLGK*

Fig. 7C: Light chain immunoglobulin DNA sequence: (SEQ ID NO: 10)

GATATTGTTCTCACCCAGACTCCAGCTTCTTTGGCTGTGTCTCTAGGGCAGAGGGCCACCATCTCCTGC
AAGGCCAGCCAAAGTGTTGATTATGATGGTGATAGTTATATGAACTGGTACCAACAGAAACCAGGACA
GCCACCCAAACTCCTCATCTATGCTGCATCCAATCTAGAATCTGGGATCCCAGCCAGGTTTAGTGGCAG
TGGGTCTGGGACAGACTTCACCCTCAACATCCATCCTGTGGAGGAGGAGGATGCTGCAACCTATTACT
GTCAGCAAAGTAATGAGGATCCATTCACGTTCGGAGGTGGGACAAAATTGGAAATAAAACGACGGGCT
GATGCTGCACCAACTGTATCCATCTTCCCACCATCCAGTGAGCAGTTAACATCTGGAGGTGCCTCAGTCGTGT
GCTTCTTGAACAACTTCTACCCCAAAGACATCAATGTCAAGTGGAAGATTGATGGCAGTGAACGACAAAATG
GCGTCCTGAACAGTTGGACTGATCAGGACAGCAAAGACAGCACCTACAGCATGAGCAGCACCCTCACGTTGA
CCAAGGACGAGTATGAACGACATAACAGCTATACCTGTGAGGCCACTCACAAGACATCAACTTCACCCATTG
TCAAGAGCTTCAACAGGAATGAGTGTTAA

Figure 7 (Continued)

Fig. 7D: Light Chain Translated sequence: (SEQ ID NO: 11)

DIVLTQTPASLAVSLGQRATISCKASQSVDYDGDSYMNWYQQKPGQPPKLLIYAASNLESGIPARFSGSGSGT
DFTLNIHPVEEEDAATYYCQQSNEDPFTFGGGTKLEIKRRADAAPTVSIFPPSSEQLTSGGASVVCFLNNFYPKD
INVKWKIDGSERQNGVLNSWTDQDSKDSTYSMSSTLTLTKDEYERHNSYTCEATHKTSTSPIVKSFNRNEC*

Figure 13

VH region

QVQLQQSGPELVKPGASVKMSCKASGYTFTNYVIHWVKQKPGQGLEWIGYINPYSDGSKYNEKFK

GKATLTSDESSSTAYMELSSLTSEDSAVYYCARGKNTEWFPYWGQSTTVTVSS — AKTTAPSVYP

CH1 region

LAPVCGDTTGSSVTLGCLVKGYFPEPVTLTWNSGSLSSGVHTFPAVLQSDLYTLSSSVTVTSSTW hinge

PSQSITCNVAHPASSTKVDKKI — EPRGPTIKPCPPCKCP — APNLLGGPSVFIFPPKIKDVLMIS

CH2 region

LSPIVTCVVVDVSEDDPDVQISWFVNNVEVHTAQTQTHREDYNSTLRVVSALPIQHQDWMSGKEF

CH3 region

KCKVNNKDLPAPIERRTISKPK — GSVRAPQVYVLPPPEEEMTKKQVTLTCMVTDFMPEDIYVEWTN

NGKTELNYKNTEPVLDSDGSYFMYSKLRVEKKNWVERNSYSCSVVHEGLHNHHTTKKSISRSLGK — murine IgD Transmembrane (TM) sequence

GIVNTIQHSCIMDEQSDSYMDLEENGLWPTMCTFVALFLTLLYSGFVTFIKVK*

(SEQ ID NO: 12)

Figure 14

CH1 region

QVQLQQSGPELVKPGASVRMSCKASGYTFTNYVTHWVKQKPGQGLEWIGYINPYSDGSKYNEKFK

GKATLTSDESSSTAYMELSSLASEDSAVYYCARGKNTEWFPYWGQGTTVTVSS – GDKREPDNFLL

*hinge region*

SECKAPEENEKINLGCLVIGSQPLKISWEPKKSSTVEHVFPSEMFPNGNYTMVLQVTVLASEINLN

HTCTINKPKRKEKPFEP – ESWDSQSSRVTPTLQAPNHSTEATKAITTKDIE – GRMAPS

CH3 region

NLTVNLLTSTHPEMSSWLLCEVSGFFPENIHLMWLGVHSKMKSTNFVTANPTAQESGTFQTWSV

*TM sequence*

LRLPVALSSSLDTYTCVVEHEASKTKLNASKSLAISG – IVNTIQHSCIMDEQSDSYMDLEEN

GLWPTMCTEVALELFLTELLYSGEVTFIKVK (SEQ ID NO: 13)

Figure 15

VH region
QVQLQQSGPELVKPGASVRMSCKASGYTFTNYVTHWVKQKPGQGLEWIGYINPYSDGSKYNEKFKGKAT

LTSDESSSTAYMELSSLTSEDSAVYYCARGKTEWPYWGQGTTVTVSS - AKTTAPSVYPLAPVCGDTT

CH1 region
GSSVTLGCLVKGYFPEPVTLTWNSGSLSSGVHTFPAVLQSDLYTLSSSVTVTSSTWPSQSITCNVAHPA hinge region
SSTKVDKKI — EPRGPTIKPCPPCKCPAP — *GERVQLAHHFSEPE* — Glycophorin A C terminal sequence
ITLIFGVMAGVIGTILLI —
*Transmembrane region*

*SYGIRRLIKKSPSDVKPLPSPDTDVPLSSVEIENPETSDQ*\*

(SEQ ID NO: 14)

Figure 16

VH Region

QVQLQQSGPELVKPGASVKMSCKASGYTFTNYVTHWVKQKPGQGLEWIGYINPYSDGSKYNEKFKGKAT

LTTSDESSSTAYMELSSLTSEDSAVYYCARGKTEMFPYWGQGTTVTVSS — AKTTAPSVYPLAPVCGDTT

CH1 Region

GSSVTLGCLVKGYFPEPVTLTWNSGSLSSGVHTFPAVLQSDLYTLSSSVTVTSSTWPSQSITCNVAHPA

*GPI Signal*

SSTKVDKKI — EPRGPTIKPCPPCKCPAP — _LTTSGIVTMSHQALG_ — FTLIGLLGTLVTMGLLT*

*DAF Sequence*

(SEQ ID NO: 15)

CELL LINES EXPRESSING SURFACE BOUND ANTI-IDIOTYPE ANTIBODIES AGAINST ANTI-CD22 ANTIBODIES AND USES THEREOF

PRIORITY

The instant application is a divisional of U.S. application Ser. No. 14/407,988 filed Dec. 15, 2014, which corresponds to the U.S. national phase of International Application No. PCT/US2013/046053, filed Jun. 16, 2013, which, in turn, claims the benefit of U.S. Provisional Application Ser. No. 61/660,327 filed Jun. 15, 2012, the entire contents of which are hereby incorporated by reference herein.

SEQUENCE LISTING

The instant application contains a Sequence Listing that has been submitted in ASCII format via EFS-Web and is hereby incorporated by reference in its entirety. Said ASCII copy, created on Jun. 16, 2013, is named SBL005PCT_ST25.txt and is 34,363 bytes in size.

BACKGROUND OF THE INVENTION

Targeted therapy by monoclonal antibody (MAb) was an old and simple concept, yet it took a combination of a variety of technologies, including antibody engineering, cell line enhancement, production, purification, formulation, and different QC assay methods to realize the long awaited clinical and therapeutic promises of the "magic bullet." To date, there are hundreds, if not thousands, of therapeutic MAbs in different stages of clinical trials against a plethora of disease indications. Along with it comes a whole host of different ideas, technologies and know how based on, or derived from MAbs with the hope of expanding the scope of their applications.

One of its ramifications is based on Network Theory, which was proposed by Niels Jerne in 1974 (Jerne N K: Towards a network theory of the immune system. Ann Immunol (Paris) 1974, 125C:373-389). Jerne suggested that the immune system is a network of interacting idiotypes that is involved in the regulation of immune responses. The concept was later evolved into the development of anti-iditotypic antibodies for different applications. Anti-idiotypic antibodies, commonly referred to as Ab2, are those antibodies raised against the immunizing antibodies (Ab1), and demonstrated specific binding against the idiotopes (unique antigenic determinants on the surface of the antibodies) of Ab1. Ab2 can be classified into three distinct groups: (1) Ab2α antibodies are those that recognize idiotopes distinct from the antigen-binding site (ABS) on primary Ab1 antibodies; (2) Ab2β antibodies recognize epitopes within the ABS and mimic the structure, and forming the so-called "internal image," of the nominal antigen; (3) Ab2γ antibodies recognize epitopes within the ABS without the structural resemblance of the nominal antigen (Pan et al. 1995. Anti-idiotypic antibodies: biological function and structural studies. Faseb J 9:43-49).

Although Ab2β antibodies appear to be the most intriguing group of Ab2 antibodies, especially attempts to use Ab2β as surrogate antigens for the development of active vaccines against autologous and/or inert antigens such as tumor-specific or tumor associated antigens, in addition to bacterial, viral and parasitic infections (Chatterjee et al. 2001. The anti-idiotype vaccines for immunotherapy. Curr Opin Mol Ther 3(1):63-69), development of other types of Ab2 can be useful in developing assay methods that facilitate the production process and clinical evaluation of a potentially therapeutic Ab1.

SM03 is a chimeric anti-CD22 antibody derived from the murine RFB4 antibody (Yang et al. 2006. Construction and characterization of recombinant anti-B-lymphoma chimeric antibody. Chinese J New Drugs 15(3):186-192), and is being used in clinical trials for the treatment of non-Hodgkin's lymphoma (NHL) (Li et al. 2012. Pharmacokinetics and tolerability of human mouse chimeric anti-CD22 MAb in Chinese patients with CD22-positive non-Hodgkin's lymphoma. Landes Bioscience J 4(2):256-266). Since SM03 targets and suppresses matured B cells, the antibody has expanded its indications for the treatment of other autoimmune diseases, such as, among others, Rheumatoid arthritis (RA) and Systemic Lupus Erythamatosus (SLE).

In order to improve the utility of "the anti-CD22 antibody," SM03 was humanized using the technology of framework-patching (Liang et al. 2006. Framework-reengineering and its application in humanized antibody fSM03. Chinese J New Drugs 15(21):1832-1836; Leung, S. O. Reducing Immunogenicities of Immunoglobulins by Framework-patching. U.S. Pat. No. 7,338,659 B2; Leung, S. O. Framework-patched Immunoglobulins. U.S. Pat. No. 7,321,026 B2). The framework-patched SM03 was later renamed as SM06. Both SM03 and SM06 target the same epitope of the human CD22 antigen, with comparable affinity. However, in terms of sequence and structure, the only thing SM03 and SM06 share in common is their ABSs, formed by their respective complementarily determining region (CDR) sequences.

SM03 and SM06 bind to human CD22 antigen. The antigen is expressed on the surface of matured B cells (Schwartz-Albiez et al. 1991. CD22 antigen: biosynthesis, glycosylation and surface expression of a B lymphocyte protein involved in B cell activation and adhesion. Int Immunol 3:623-633; Stoddart et al. 1997. Analysis of murine CD22 during B cell development: CD22 is expressed on B cell progenitors prior to IgM. Int Immunol 9:1571-1579), and upon binding to the antigen, the antibody-antigen complex is rapidly internalized (Yang et al. 2006; Liang et al. 2006). This has made the development of a biological assay to evaluate the bioactivities of SM03 and SM06 difficult. The same problem applies to other antibodies that target internalizing antigens, such as invariant chain, CD33, Lewis Y antigen, etc. Moreover, convenient and robust methods in evaluating the level of circulating SM03 and SM06 (as well as RFB4) and their derivatives (scoff, Fab, diabodies, immunotoxins, drug conjugates, etc.) are needed for the evaluation of serum half-lives for these products during pharmacokinetic studies. Since soluble CD22 is not widely available, and exogenous CD22 tends to be less stable, the availability of an anti-idiotype antibody against SM03 and its derivatives will be extremely useful for such purposes.

The present invention is therefore directed to the use of anti-idiotypes in immunotherapy trials as diagnostic reagents for monitoring the pharmacokinetics (PK) of the administered antibody in the circulation of patients. The anti-idiotype antibody can similarly be used as a positive control for HAHA, HACA or HAMA immune responses to the administered antibody. Monitoring the presence of such immune responses will influence treatment options as such immune responses may affect the clinical outcome in patients (Gruber, van Haarlem et al. 2000. The human anti-mouse immunoglobulin response and the anti-idiotypic network have no influence on clinical outcome in patients with minimal residual colorectal cancer treated with monoclonal antibody CO17-1A. Cancer Res. 60:1921-1926), or can be associated with undesirable hypersensitive reactions and dramatic changes in PK and biodistribution of the administered antibody.

Another embodiment of the present invention is to provide a general method for the evaluation of biological functions of antibodies that target internalizing antigens, including, CD22, Invariant Chain (CD74), CD33, Lewis Y antigen, etc. The method includes the construction of an engineered cell line that expresses on their surface a non-internalizing fusion protein containing the anti-idiotype binding moiety. In the present invention, the cell line that expresses surface anti-SM03 anti-idiotype antibody (or antibody fragment fusion) can be used for the evaluation of the biologic activity of SM03 and SM06 via complement-dependent cytotoxicity (CDC) or antibody directed cell cytotoxicity (ADCC) as a quality control measure.

SUMMARY OF THE INVENTION

The present invention describes the generation and production of an anti-idiotype antibody that recognizes the antigen-binding site (ABS) of an anti-CD22 antibody and their derivatives (including the murine, chimeric and humanized version of the antibodies and their derivatives such as scFv, diabodies, bispecific antibodies, antibody conjugate, and antibody fusion proteins, etc.), a class collectively referred to as "the anti-CD22 antibodies". The present invention further describes the use of such anti-idiotype antibodies for the development of assay methods to evaluate the identity, binding affinity, biological activities, and serum concentration of "the anti-CD22 antibodies" during clinical trials.

One aspect of the invention is to provide anti-idiotype antibodies specific for "the anti-CD22 antibodies". Another aspect of the invention is to provide anti-idiotype antibodies which bind to the variable region of "the anti-CD22 antibodies." Yet another aspect of the invention is to provide anti-idiotype antibodies which bind to the ABS of "the anti-CD22 antibodies." Similarly, another aspect of the invention is an anti-idiotype antibody which blocks the binding of an anti-CD22 MAb to its nominal (CD22) antigen. Another aspect of the invention is to provide an anti-idiotype antibody which specifically binds RFB4, a murine antibody. Similarly, a further aspect of the invention is to provide an anti-idiotype antibody which specifically binds SM03, a chimeric antibody. Yet a further aspect of the invention is to provide an anti-idiotype antibody which specifically binds SM06, a humanized antibody using the framework-patching technology. Specifically, the anti-idiotype antibodies provided for in this invention can be selected from the group consisting of a murine MAb, a chimeric antibody, a human antibody, a humanized antibody, a single chain antibody, or a disbud, and other forms of fusion proteins.

Another aspect of the invention is to provide a transfected cell line capable of producing an ant-idiotype antibody specific for "the anti-CD22 antibodies." A further aspect of the invention is to provide a cell line producing an anti-idiotype antibody which is specific for "the anti-CD22 antibodies" selected from the group consisting of RFB4 (murine antibody), SM03 (chimeric antibody) and SM06 (framework-patched antibody).

Another embodiment of the invention is to provide methods for detecting the ability of an anti-idiotype antibody to inhibit the binding of antibody to antigen. A further aspect of the invention is to provide methods for detecting the ability of anti-idiotype antibodies to capture and detect bound idiotype antibody Another aspect of the invention is to provide methods for detecting the ability of anti-idiotype antibody to bind to "the anti-CD22 antibodies." Another aspect of the invention is to provide methods of detecting the amount of "the anti-CD22 antibodies" in sample serum.

The present invention is also directed against a method to detect HAMA, HACA and HAHA responses using the antibody of the invention.

Another aspect of the present invention is to provide an engineered cell line with surface expression of the binding moiety of the anti-idiotype antibody. A further aspect of the invention is directed against a method to assess the biological activities of "the anti-CD22 antibodies" using the engineered cell lines as target cells for CDC and/or ADCC assays.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention.

It will also be understood that both the foregoing summary of the present invention and the following detailed description are of exemplified embodiments, and are thus not restrictive of the present invention or other alternate embodiments of the present invention. Other objects and features of the invention will become more fully apparent when the following detailed description is read in conjunction with the accompanying figures and examples. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE FIGURES

Various aspects and applications of the present invention will become apparent to the skilled artisan upon consideration of the brief description of the figures and the detailed description of the present invention and its preferred embodiments that follows:

FIG. 2 depicts the complementarity determining region (CDR) sequences of three selected scFv phages (Phage #1-3) interacted with RFB4, SM03 and SM06 (murine, chimeric and humanized versions) but not with other antibody (anti-TNF) and control protein (BSA). Since the only sequence in common between murine RFB4, SM03, and SM06 would be in the CDR sequences, or the antigen binding region, of the target antibodies, these results suggested that all three selected scFv phages were specific for the idiotype of SM03. FIG. 2A depicts the heavy chain CDR sequences, SEQ ID NOs: 1-3, and FIG. 2B depicts the light chain CDR sequences, SEQ ID NOs: 4-6, for the scFv phages #1-3, referred to as CDR1, CDR2, and CDR3, respectively. Antibodies are identical, except for a single amino acid sequence difference (underlined) in the CDR3 region of the light chain in phage #2 (CDR3-2).

FIG. 3 depicts the amino acid sequence (single letter code, SEQ ID NO: 7) of scFv isolated from phage #3 which showed specific binding to RFB4, SM03 and SM06. CDR sequences are boxed. The configuration of the scFv is VH-linker-VL. The linker sequence (shown in italics) used is $G_4$-S-G-S-G-S-S-$G_4$ (SEQ ID NO: 16).

FIG. 7 depicts cDNA sequences for the heavy (FIG. 7A) and light (FIG. 7C) immunoglobulin chains of the "anti-idiotype mIgG" expressed in clone AE6 using standard RT-PCR and Sanger's dideoxynucleotide sequencing procedures. The deduced amino acid sequences in single-letter code of the respective chains are also shown, in FIGS. 7B and 7D respectively.

FIG. 13 depicts the structure and amino acid sequence (SEQ ID NO: 12) of the heavy chain of the "anti-idiotype mIgG" fused to the transmembrane (TM) sequence of murine IgD.

FIG. 14 depicts the structure and amino acid sequence (SEQ ID NO: 13) of the "anti-idiotype mIgG" carrying murine IgD heavy chain (TM sequence underlined).

FIG. 15 depicts the structure and amino acid sequence (SEQ ID NO: 14) of the "anti-idiotype mIgG" Fd-glycophorin A fusion protein.

FIG. 16 depicts the structure and amino acid sequence (SEQ ID NO: 15) of the "anti-idiotype mIgG" Fd-GPI fusion.

DETAILED DESCRIPTION OF THE INVENTION

Figure 1:
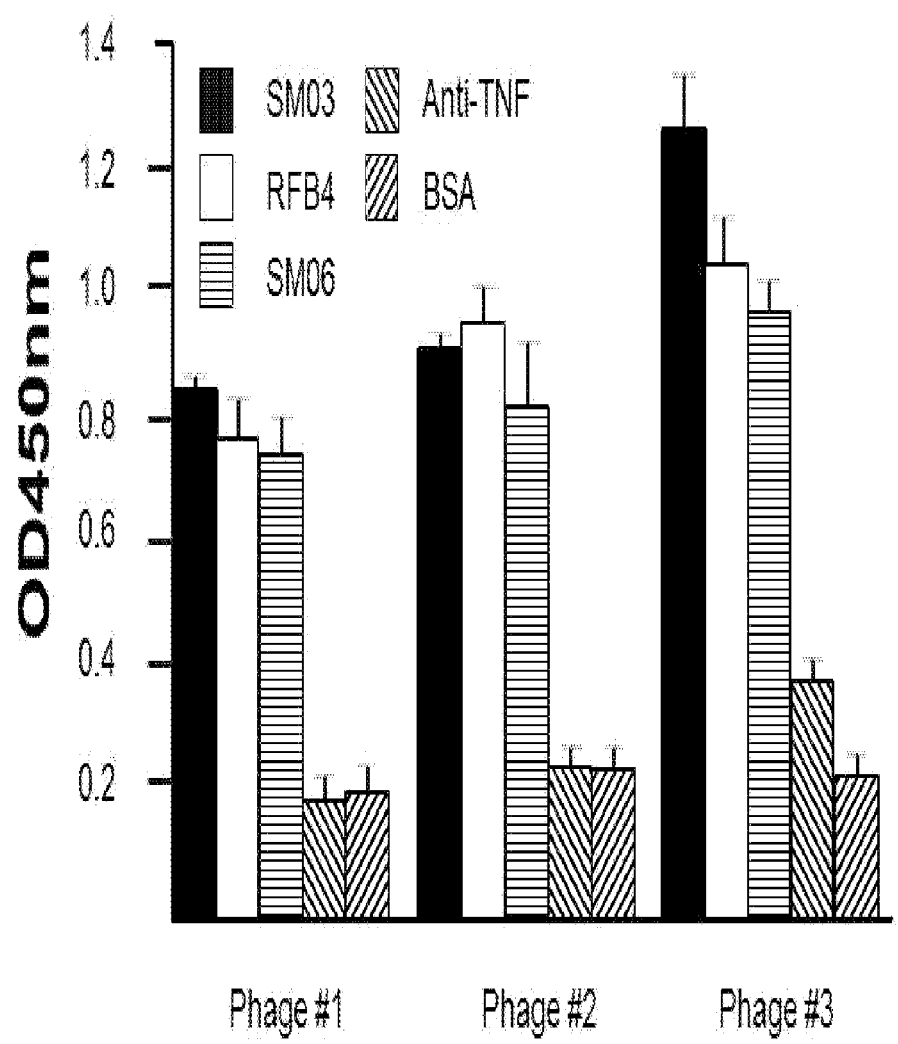
FIG. 1 depicts the specific binding of different scFv Phages (Phages #1-3) against murine (RFB4), chimeric (SM03) and framework-patched (SM06) anti-CD22 antibodies. The phages do not exhibit significant binding against a control anti-TNF antibody (chimeric) and BSA.

This invention describes the generation, production and use of anti-idiotype antibody and its derivatives for anti-CD22 MAbs. The anti-CD22 MAbs described herein refer to murine, chimeric, humanized (framework-patched) antibodies and their derivatives, including but not limited to, antibody fragments (Fab, Fab', F(ab')$_2$), scFv, diabodies, bispecific antibodies, and antibody fusion proteins, etc., and are collectively referred to hereinafter as "the anti-CD22 antibodies." Specifically, the present invention provides an anti-idiotype antibody whose binding moiety interacts specifically to the variable regions of the "anti-CD22 antibodies". More specifically, it provides an anti-idiotype antibody whose binding moiety interacts specifically to the ABS of "the anti-CD22 antibodies." One embodiment of the invention is an anti-idiotype antibody, which effectively inhibits the binding of "the anti-CD22 antibodies" to its natural ligand (human CD22). Specifically, another aspect of the invention is to provide an anti-idiotype antibody, which binds the anti-CD22 MAb, RFB4. Additionally, it provides an anti-idiotype antibody, which binds the anti-CD22 chimeric antibody, SM03 (Yang et al. 2006. Construction and characterization of recombinant anti-B-lymphoma chimeric antibody. Chinese J New Drugs 15(3):186-192). Similarly, another aspect of the invention is to provide an anti-idiotype antibody, which binds the anti-CD22 antibody humanized by framework-patching, SM06 (also named as fSM03) (Liang et al. 2006. Framework-reengineering and its application in humanized antibody fSM03. Chinese J New Drugs 15(21):1832-1836). The anti-idiotype antibodies provided for in this invention can be selected from the group consisting of a MAb of murine isotypes, a chimeric antibody, a human antibody, a humanized or framework-patched antibody, a single chain antibody, diabody, bispecific antibody and other antibody fusion proteins.

Another embodiment of the present invention is to provide a transfectoma capable of producing an anti-idiotype antibody specific for "the anti-CD22 antibodies".

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

Unless otherwise defined, all technical and scientific terms used herein have the same meaning as commonly understood by one of ordinary skill in the art to which this invention belongs. In case of conflict, the present specification, including definitions, will control.

Definitions:

As used herein, the term "immunoglobulin" refers to a protein molecule consisting of one or more polypeptides substantially encoded by immunoglobulin genes. The recognized immunoglobulin genes include the kappa, lambda, alpha, gamma (IgG1, IgG2, IgG3, IgG4), delta, epsilon and mu constant region genes, as well as the myriad immunoglobulin variable region genes. Full length immunoglobulin "light chains" (about 25 Kd or 214 amino acids) are encoded by a variable region gene at the $NH_2$-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

Unless indicated otherwise, as used herein, the term "antibody" is used broadly to refer to both antibody molecules and its derivatives. Such derivatives contain at least one variable region from either a heavy or light immunoglobulin chain, and should encompass molecules such as antibody fragments in the form of $F(ab')_2$, Fab, Fab', Fd, Fabc, scFv, diabodies, individual antibody light chains, individual antibody heavy chains, chimeric fusions between antibody chains, bispecific antibodies and other molecules, and the like.

The term "variable region" as used herein in reference to immunoglobulin molecules has the ordinary meaning given to the term by the person skilled in the art of immunology. Both antibody heavy and light chains may be divided into a "variable region" and a "constant region". The person skill in the art may readily distinguish a variable region from a constant region by reference to standard tests describing antibody structure, e.g., Kabat et al. 1991. "Sequences of Proteins of Immunological Interest: $5^{th}$ Edition" US Department of Health and Human Services, US Government Printing Office.

The term "chimeric" antibody refers to a reengineered protein molecule with the heavy and light chain variable region sequences derived from non-human species, while the constant region sequences are derived from human immunoglobulin.

The term "humanized" antibody refers to a reengineered protein molecule with all its CDRs (complementarity determining regions) derived from the variable region sequences of immunoglobulin that is of non-human species origins, while the majority of the remainder of the sequences are derived from a human immunoglobulin.

The term "idiotype" as used herein refers to the segment of an antibody molecule that determines its specificity for antigen. The idiotype is located in the Fab region, and its expression usually requires participation of the variable regions of both heavy and light chains that form the antigen-combining site.

The term "antigen-binding site" as used herein refers to the region(s) of an antibody molecule to which a ligand actually binds, and is derived from an antibody; the term "antigen-binding site" include antibody heavy chain variable domains (VH) and/or an antibody light chain variable domains (VL), or pairs of VH/VL, and can be derived from whole antibodies or antibody fragments such as single chain Fv, a VH domain and/or a VL domain, Fab, or (Fab)2. In one embodiment of the current invention each of the antigen-binding sites comprises an antibody heavy chain variable domain (VH) and/or an antibody light chain variable domain (VL), and preferably is formed by a pair consisting of an antibody light chain variable domain (VL) and an antibody heavy chain variable domain (VH).

The term "isotype" as used herein refers to antigens that determine the class or subclass of heavy chains or the type and subtype of light chains of immunoglobulin molecules. For example, the four isotypes of IgG are designated IgG1, IgG2, IgG3 and IgG4.

Human CD22 antigens are expressed on the surface of mature B cells and malignant B cells (Dröken et al. 1989. B-cell antigens: CD22. In Knapp et al., eds. Leucocyte Typing IV: White cell differentiation antigens. New York, Oxford University Press. P.63-64). CD22 is a regulatory molecule that prevents the over activation of the immune system and the development of autoimmune diseases (Hatta et al. 1999. Identification of the gene variations in human CD22. Immunogenetics 49(4):280-286). One of "the anti-CD22 antibodies" described herein is derived from the murine antibody RFB4. It's chimeric (SM03) and humanized (SM06) versions, like their murine counterpart, specifically target the B epitope of the human CD22 antigen. Clinical trials for the treatment of B-cell lymphoma and other autoimmune diseases with SM03 are underway. In the determination of serum levels of "the anti-CD22 antibodies" such as SM03, administered during the clinical studies, anti-idiotype antibodies were generated and characterized for suitability as ELISA reagents for measuring "the anti-CD22 antibodies" in patient sera samples. Moreover, the anti-idiotype antibody thus generated can be used for the development of ELISA reagents for measuring HACA or HAHA responses, either as control antibodies or as diagnostic agent to evaluate the presence of competing antibodies in patient serum.

The anti-idiotype antibody was generated from mice immunized with SM03 using phage display technologies. Specifically, messenger RNA were isolated from splenocytes of mice immunized with the anti-CD22 chimeric antibody, SM03, and degenerate variable region flanking primers used to amplify heavy and light chain variable region sequences which were subsequently incorporated into a scFv phage display libraries following standard procedure. Upon several rounds of panning with SM03 and RFB4, antibody phages that showed binding against SM03, RFB4 and SM06 were identified, and the variable region sequences of the respective phages elucidated. The variable region sequences of the antibody phage that demonstrated the highest affinity against murine, chimeric and humanized forms of "the anti-CD22 antibodies" were selected.

Initially, the anti-idiotype antibody sequence was overexpressed in E. coli as scFv inclusion bodies, which were subsequently denaturated and refolded; the active scFv was used to develop ELISA reagents for the detection of serum levels of SM03 in clinical trial. Briefly, refolded scFv anti-idiotype antibody was used to coat ELISA plate, and serum from patients treated with SM03 was added, incubated, and the wells washed. SM03 present in the serum would bind to the coated anti-idiotype scFv, and could be revealed by the addition of HRP-conjugated goat anti-human Fc-specific antibody (Jackson ImmunoResearch, West Grove, Pa.). However, the anti-idiotype scFv tends to be unstable, and production from bacterial inclusion bodies could result in variations in the quality of the denatured and refolded proteins, making the results inconsistent. Moreover, due to the unstable nature of the anti-idiotype scFv, it would make storage, and therefore preparation of validated batches for the anti-idiotype scFv difficult.

Full immunoglobulin molecules, on the other hand, are known to be stable, when stored under appropriate conditions, for months, if not years, without significant changes in the quality of the antibody. In order to establish stable and consistent assay reagents for evaluating serum anti-CD22 antibodies and probably HACA and HAHA responses, the variable region sequences of the anti-idiotype scFv were used to construct a full length immunoglobulin molecule. As the chimeric or humanized versions of "the anti-CD22 antibodies" both carry human IgG1 and kappa constant region sequences, they can be detected by standard HRP-conjugated anti-human Fc antibodies (or similar conjugates). It is therefore important that the anti-idiotype immunoglobulin should not carry constant region sequences that might cross-react with the detecting conjugates. Murine IgG2a/kappa constant regions do not cross react with anti-human Fc antibodies, and are therefore chosen for constructing full immunoglobulin for the anti-idiotype antibody. It should be noted, however, constant region sequences of different isotypes and from different species can also be used. Cell lines that produced over 30 μg/ml of the anti-idiotype antibody with the murine IgG2a/kappa ("anti-idiotype mIgG") were generated. Since the expression vector employed for generating the cell lines contains an amplifiable dihydrofolate reductase (DHFR) gene, such yields, if needed, can be further enhanced through standard amplification and cloning procedures. Nevertheless, the current yield is sufficient for the purpose of producing consistent batches of "anti-idiotype mIgG" as reagents for pharmacokinetic and HACA or HAHA assays. Briefly, "anti-idiotype mIgG" was used to coat ELISA plates. Sera from patients treated with "the anti-CD22 antibodies" were added; after incubation, proteins not captured by the coated "anti-idiotype mIgG" were washed off. Serum anti-CD22 antibodies that interacted with the coated "anti-idiotype mIgG" was revealed by the addition of HRP-conjugated goat anti-human-Fc-specific antibody (Jackson ImmunoResearch). Since murine constant region of the "anti-idiotype mIgG" do not cross react with the detecting HRP conjugate, the assay does not result in problems with background signals. The assay method was proven to be highly reproducible, sensitive, and specific. The same method can be extrapolated for use to evaluate the identity, and affinity of "the anti-CD22 antibodies." Establishment of HACA and HAHA analysis of sera samples by BIAcore was possible using the "anti-idiotype mIgG" as positive controls for quantitation of immune responses in patient sera and the "anti-idiotype mIgG" could also be used to study the penetrance and binding of "the anti-CD22 antibodies" to tumor cells through immunohistochemical analysis of tumor biopsies. The generation of "anti-idiotype mIgG" capable of specifically binding a target antibody provides reagents with high sensitivity for the assessment of safety and pharmacokinetic profiles of target antibodies administered clinically. "Anti-idiotype mIgG" thus generated in the present invention had proved useful as diagnostic laboratory reagents for studying clinical samples from patients receiving SM03 immunotherapy.

One aspect of the present invention provides methods for detecting the ability of an "anti-idiotype mIgG" to inhibit the binding of "the anti-CD22 antibodies" to antigen. Another aspect of the invention is to provide methods for detecting the ability of the "anti-idiotype mIgG" to capture and detect bound idiotype antibody. A further aspect of the invention is to provide methods for detecting the ability of "anti-idiotype mIgG" to bind to idiotype (anti-CD22) antibody. Yet another aspect of the invention is to provide methods of detecting the amount of "the anti-CD22 antibodies" in sample serum. The present invention is also directed against a method to detect HAMA, HACA and HAHA responses using the antibody of the invention.

One other aspect of the current invention is to make use of the anti-idiotype antibody to construct cell lines that express the SM03-specific binding moieties of the anti-idiotype antibody in different forms or as fusion proteins on the cell surface in a non-internalizing mode. The cell lines developed can be used for the establishment of biological assays to evaluate the bioactivities of SM03 and/or its derivatives such as RFB4 and SM06, etc. The method is meant to confer a general applicability for the evaluation of biological activities of antibodies that bind to internalizing surface antigens.

Hereinafter, the present invention is described in more detail with reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Example 1

Obtaining VL and VH Sequences of an Anti-SM03 Anti-Idiotype Antibody by Phage Display Library
Preparation of Phage-Display Library from Mice Immunized with SM03

Female BALB/c mice of ~6 weeks old were immunized intra-peritoneally with 100 μg of SM03, which was emulsified in 200 μl of complete Freund's adjuvant (Sigma-Aldrich, St. Louis, Mo.) following a standard immunization protocol (Harlow and Lane, 1988. In Antibodies: A Laboratory Manual. New York, Cold Spring Harbor Laboratory). Secondary and tertiary immunizations were carried out at intervals of 14, and 35 days by intra-peritoneal injection of 100 μg of SM03 emulsified in 200 μl of incomplete Freund's adjuvant (Sigma-Aldrich).

Anti-SM03 titer in the sera from immunized mice were determined (data not shown). Total RNA from the spleen of immunized mice (day 39 post immunization) was extracted for cDNA preparation (Superscript II, Invitrogen, Grand Island, N.Y.). PCR amplification of immunoglobulin variable regions was performed using degenerate primers as described in Cheng et al. (Cheng et al. 2005. Cross-reactivity of antibody against SARS-coronavirus nucleocapsid protein with IL-11. Biochem Biophys Res Commun 338(3):1654-60). Phage library displaying scFv was constructed using Amersham's recombinant phage antibody system (Amersham, Piscataway, N.J.) according to manufacturer's specifications.

Propagation of scFv-phage display library and filamentous phages was performed as previously described (McWhirter et al. 2006. Antibodies selected from combinatorial libraries block a tumor antigen that plays a key role in immunomodulation. PNAS USA 103:1041-1046). Panning was carried out first with SM03 and then with RFB4 (Ancell, Bayport, Minn.) in 4 sequential rounds in 24-well microplates (IWAKI Cell Biology, Tokyo, Japan). Briefly, phages at a concentration of $10^{12}$ were biopanned against equal amounts (100 µg/ml) of SM03 or murine RFB4 (Ancell) in carbonate coating buffer (15 mM $Na_2CO_3$, 35 mM $NaHCO_3$, pH 9.6). After incubation at room temperature for 2 h with gentle shaking, bound scFv-phages were eluted by incubation at room temperature for 10 min with 100 µl of 0.1 M glycine-HCl, pH 2.2, followed by neutralization with 10 µl of 1 M Tris-HCl, pH 8.0. The selection process was repeated four times with the input and output phage titers at each round recorded.

Phages that survived panning were rescued. The binding specificities of selected phages were evaluated by Phage-ELISA using the target anti-CD22 antibodies RFB4, SM03, and framework-patched (humanized) SM06 and other control antibodies as antigens. Briefly, into the wells of a 96-well ELISA plate (NUNC, Roskilde, Denmark) that were coated with RFB4, SM03, and SM06, chimeric anti-TNF antibody, and BSA (coated with 50 µl of carbonate coating buffer, pH 9.6, containing 1 µg of antibody/BSA; incubated at 4° C. overnight; washed three times with 200 µl of borate washing buffer, pH8.0; and blocked with borate washing buffer, pH8.0 at 37° C. for 1 h), three clones of phages that showed the highest degree of binding to SM03 (100 µl of culture supernatant) were added for incubation at 37° C. for 1 h. After washing five times with borate washing buffer, pH8.0, horse radish peroxidase (HRP)-conjugated anti-M13 mouse antibody (Amersham) at a dilution fold of 3,000 was added. After an incubation period of 1 h at 37° C., the level of anti-M13 antibody binding was revealed by the addition of 100 µl of o-phenylenediamine (Sigma) substrate solution (10 mg OPD in 10 ml of citric phosphate buffer, pH 5.0, 8 µl of 30% $H_2O_2$). The results were as shown in FIG. 1.

Results indicated that the three selected scFv phages (Phage #1-3) interacted with RFB4, SM03 and SM06 (murine, chimeric and humanized versions) but not with other antibody (anti-TNF) and control protein (BSA). Since the only sequence in common between murine RFB4, SM03, and SM06 would be in the CDR sequences, or the antigen binding region, of the target antibodies, these results suggested that all three selected scFv phages were specific for the idiotype of SM03.

Elucidation of the Variable Region Sequences of scFv Phages that Bind Specifically to the Binding Region of SM03

The scFv encoding DNA of the selected phages with demonstrated binding specificity against SM03 and its derivatives were sequenced using Sanger's method (Sanger et al. 1977. DNA sequencing with chain-terminating inhibitors. PNAS USA 74(12):5463-5467). Sequences that corresponded to antibody variable region were very similar, and differed only at sporadic positions at the framework regions or at the CDR3 segment. FIGS. 2A and 2B illustrate the CDR sequences found in the heavy and light chain sequences of the selected phages.

scFv Sequence of Phage #3 can Inhibit Binding of SM03 to Raji Cells

Due to the relatively higher binding affinity of the scFv Phage #3, the single-chain sequence was retrieved and cloned into a bacterial expression vector for scFv. The full sequence of the scFv for Phage #3 is shown in FIG. 3 (SEQ ID NO: 7). DNA sequence encoding scFv of Phage #3 was ligated into pET3 vector (Strategene, La Jolla, Calif.) and transformed into BL21(DE3)pLyS competent cells (Promega, Madison, Wis.). A His-tag was included at the C-terminus of the scFv to facilitate purification. Inclusion body containing scFv was collected after IPTG induction, and was denatured (6 M guanidine HCl in 20 mM sodium phosphate and 0.5 M NaCl, pH 7.4), refolded, and purified using HiTrap Chelating HP column according to the manufacturer's specifications (Amersham). Briefly, denatured scFv containing a His tag were bound to HiPtrap Chelating HP column with $Ni^{2+}$ added. Decreasing concentration (in gradient) of guanidine HCl in 20 mM sodium phosphate and 0.5 M NaCl, pH 7.4, was applied until all the guanidine HCl in the column was cleared. The column was washed with several bed volumes of 5-40 mM imidazole (Sigma) in 20 mM sodium phosphate and 0.5 M NaCl, pH 7.4. The eluted samples were pooled and the protein examined by SDS-PAGE electrophoresis (not shown).

Figure 4:
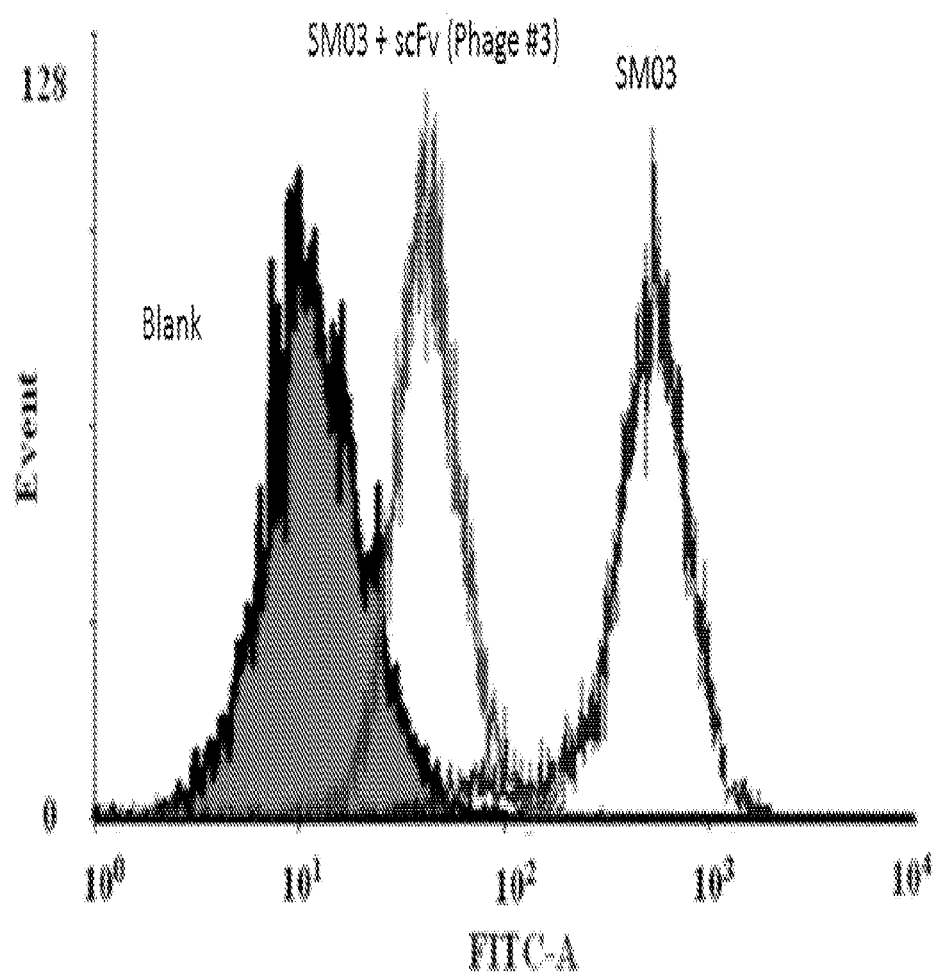
FIG. 4 graphically demonstrates how single-chain antibody (scFv) derived from phage #3 can effectively inhibit the binding of SM03 to Raji cells in a flow-cytometry assay.

The soluble scFv was used to compete with cell surface CD22 (Raji cells) for binding to SM03. At 100 µg/ml, soluble scFv derived from Phage #3 effectively inhibited the binding of SM03 onto CD22 antigen on the surface of Raji cells, as revealed by a significant reduction in fluorescence when evaluated by flow cytometry (FIG. 4).

Example 2

Use of scFv from Phage #3 to Evaluate the PK of SM03 Clinical Trials

The single-chain scFv from Phage #3 had demonstrated specificity against SM03, and can therefore be used for the development of assay method for the evaluation of blood levels of SM03 in patients treated with the anti-CD22 antibody, especially in clinical trials where pharmacokinetic (PK) studies were required. The scFv from Phage #3 was prepared as described above, and used to coat 96-well ELISA plates (NUNC). The plate was then blocked with BSA, washed, and blood samples collected at different time points from patients treated with SM03 were added. After incubation at 37° C. for 2 h, the wells were washed thoroughly, and goat anti-human Fc-specific antibody conjugated with HRP (Jackson ImmuoResearch) at a dilution of 1:4000 added. The plate was incubated for 1 h at 37° C., and washed five times before the presence of captured SM03 and its concentration were revealed by the addition of Tetramethyl Benzidine (TMB) substrate (3,3',5,5'-tetramethylbenzidine) (Invitrogen) at 450 nm in a standard ELISA assay.

Figure 5:
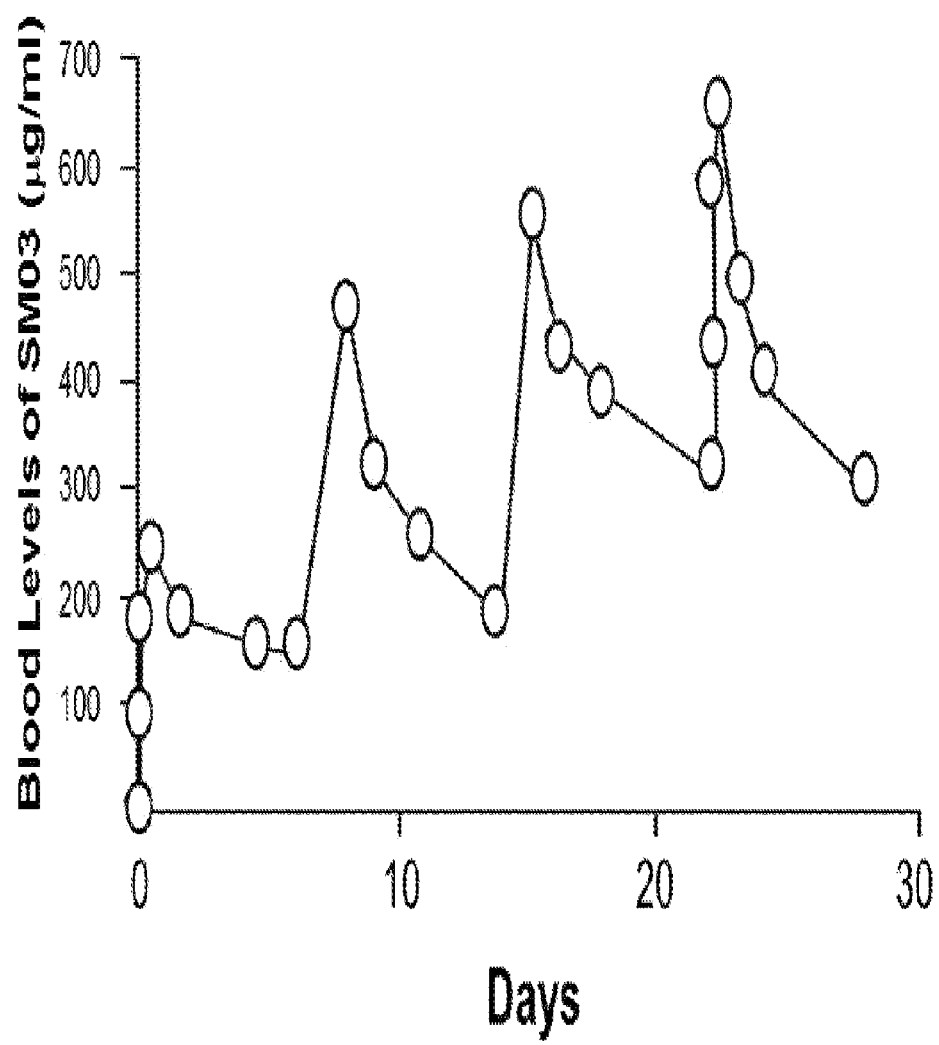
FIG. 5 depicts the pharmacokinetic profile of a lymphoma patient treated with SM03 (360 mg/m$^2$, i.v., once a week, four weeks). The serum concentration of SM03 was determined by ELISA with immobilized scFv from phage #3 as the capture antibody.

FIG. 5 showed a typical PK profile of SM03 evaluated using the aforementioned assay method in a lymphoma patient treated with the anti-CD22 antibody. SM03 was administered at 380 mg/m², once a week for four weeks. Blood samples were collected at different time points before and after SM03 administration.

Example 3

Generation of a Stable Anti-Idiotype Immunoglobulin that Binds to "the Anti-CD22 Antibodies"

Construction of Anti-Idiotype Murine Immunoglobulin (IgG2a/Kappa) Containing the VH and VL Sequences Derived from the scFv of Phage #3

Figure 6:
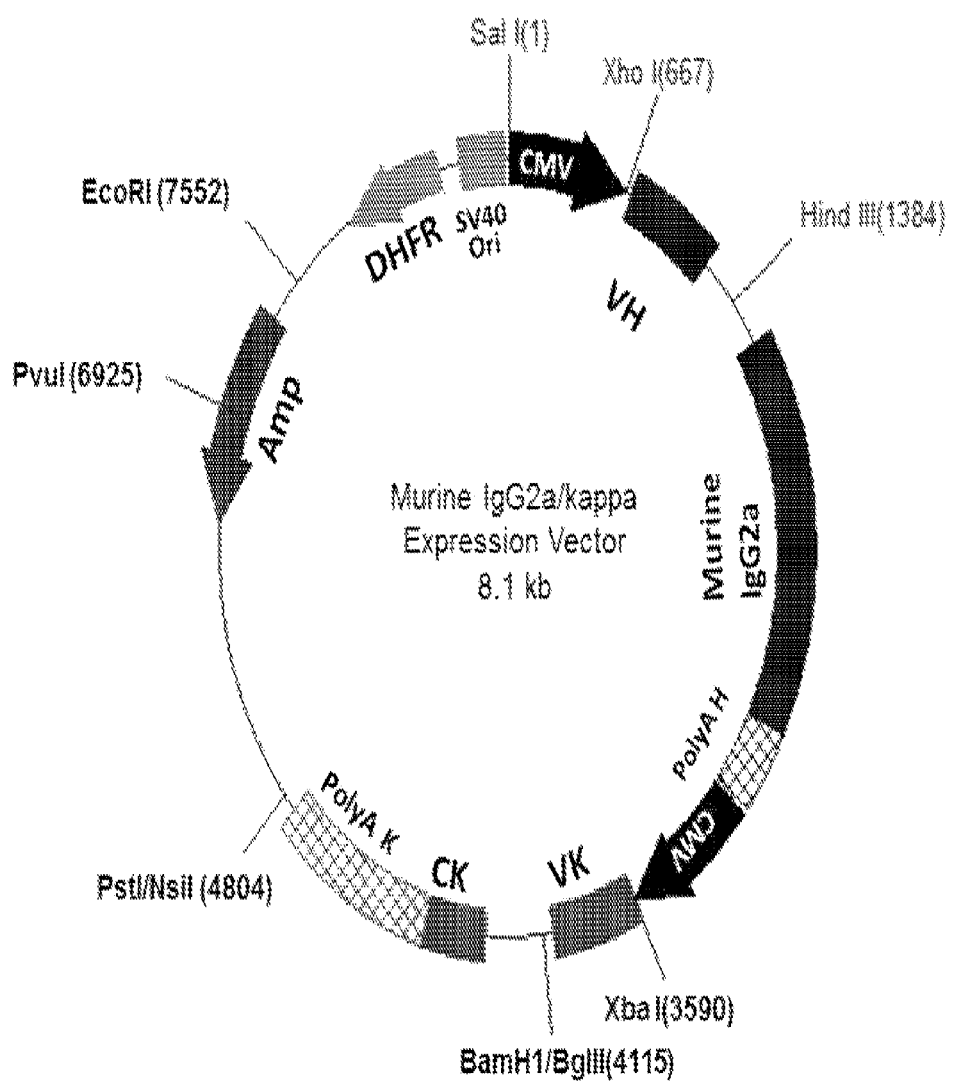
FIG. 6 depicts the amplifiable DNA vector for the expression of anti-idiotype antibody as murine IgG2a/kappa immunoglobulins.

Production of scFv from Phage #3 requires bacterial culture, induction, collection of inclusion bodies, denaturation, refolding and His-tag dependent purification. Moreover, scFv tends to be unstable upon storage. In order to generate a stable molecule with the binding properties of the scFv of Phage #3 that can be purified by standard procedure and is stable upon storage, the VH and VL sequence of the scFv of Phage #3 were PCR amplified and cloned into an amplifiable expression vector containing the murine kappa and IgG2a constant region sequences (FIG. 6).

The expression vector could be used to transfect a variety of mammalian host cell lines, including, without limitation, Chinese hamster ovary (CHO) cells, murine myeloma SP2/0 or NS0, baby hamster kidney (BHK) cells, human embryonic kidney 293 (HEK 293) cells, African green monkey kidney COS cell line, etc. Specifically, SP2/0 cells were transfected with the expression vector by electroporation following standard procedure. Clones surviving methotrexate (MTX) selection were tested for antibody expression. Clone T081210AE6 (AE6) was tested positive, and showed the highest level of expression for murine IgG. After several rounds of amplification, cell line AE6 was expanded, and the "anti-idiotype mIgG" purified. Meanwhile, RNA was prepared from AE6 and the cDNA encoding the heavy and light chain sequences of the "anti-idiotype mIgG" from AE6 were retrieved by standard RT-PCR. The cDNA sequences were elucidated by Sanger's method (Sanger et al. 1977. DNA sequencing with chain-terminating inhibitors. PNAS USA 74(12):5463-5467). Sequences were confirmed to be identical to that of a murine immunoglobulin with the IgG2a/kappa isotype and carrying the variable region sequences of the anti-SM03 scFv of Phage #3 (See FIGS. 7A-7D). "Anti-Idiotype mIgG" Purified from Clone AE6 Demonstrated Direct Binding to SM03

Figure 8:
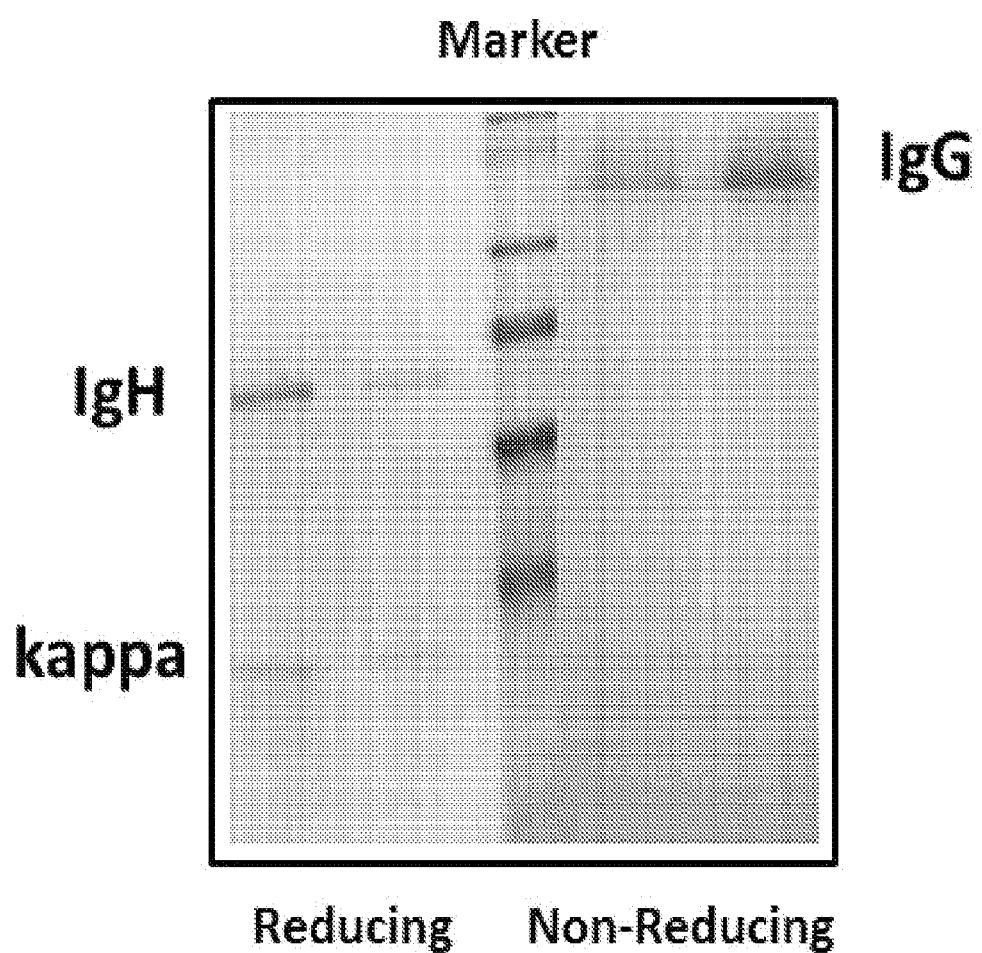
FIG. 8 depicts the results of SDS-PAGE electrophoresis showing the immunoglobulin chains of the "anti-idiotype mIgG" expressed in clone AE6 under reducing and non-reducing conditions.

Clone AE6 was expanded and antibody was purified from the culture supernatant by Protein A chromatography following standard procedure. The purified antibody was stored in PBS at 4° C. FIG. 8 showed the SDS-PAGE profile of the purified antibody under reducing and non-reducing conditions.

Figure 9:
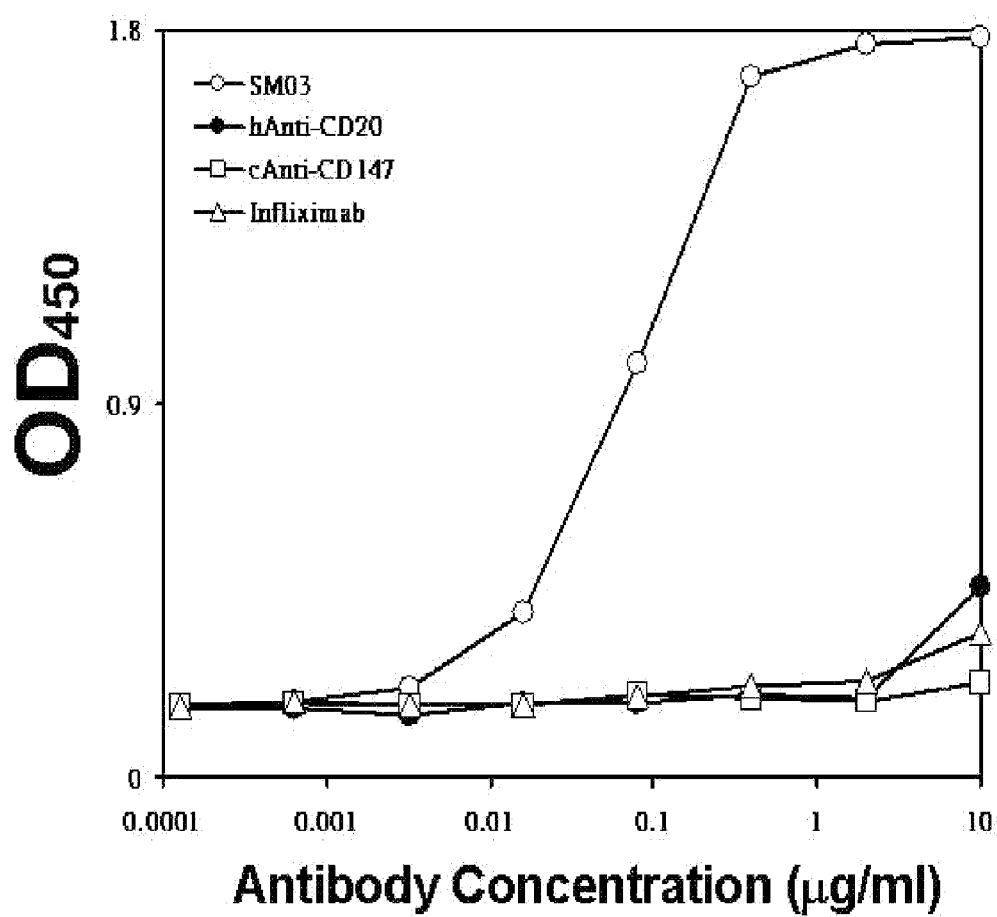
FIG. 9 demonstrates how SM03, but not other antibodies (anti-CD20, anti-CD147 and anti-TNF antibodies), specifically binds to the "anti-idiotype mIgG" purified from clone AE6.

The purified "anti-idiotype mIgG" derived from clone AE6 was used to coat ELISA plate following standard procedures. To the wells of the coated plate, 60 µl of SM03, and other irrelevant control antibodies such as anti-CD20 (humanized), anti-CD147 (chimeric), and anti-TNF (infliximab) antibodies at various concentrations were added. After an incubation period of 1.5 h at room temperature, the plate was washed three times with PBS, and HRP-conjugated goat-anti-mouse Fc-specific antibody (1:5000) (Jackson ImmunoResearch) were added. The plate was incubated at room temperature for an additional 45 min, washed three times with PBS, and binding was revealed at OD 450 nm after the addition of OPD substrate. Results indicated that the binding of the "anti-idiotype mIgG" from clone AE6 binds only to SM03 but not to other irrelevant, control antibodies (FIG. 9).

Figure 10:
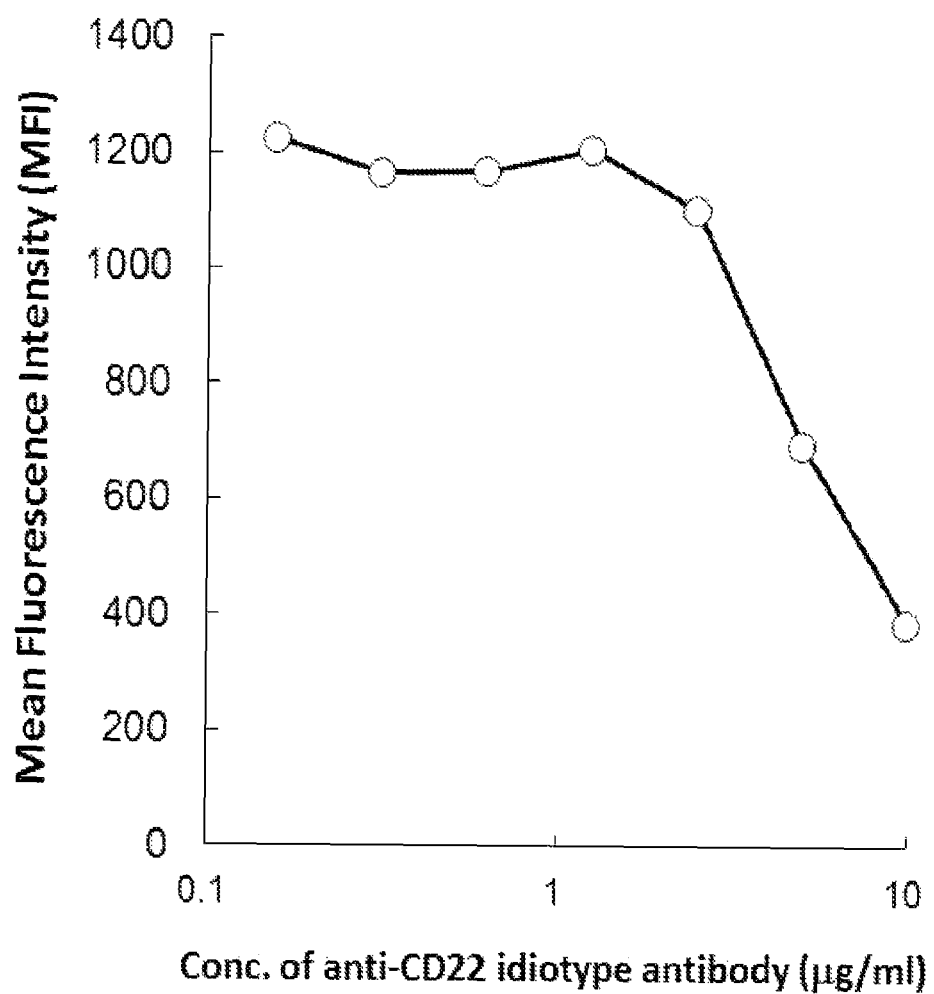
FIG. 10 depicts the results of a flow cytometry study showing that the "anti-idiotype mIgG" can effectively block the binding of SM03 on CD22 expressed on the surface of Raji cells.

To evaluate the ability of the "anti-idiotype mIgG" from clone AE6 in competing with CD22 in its natural conformation for binding to SM03, a flow cytometry study using Raji cell (human Burkitt's lymphoma) as the source of surface bound CD22 was performed. Briefly, 0.5×10$^6$ Raji cells were incubated with 1 µg/ml SM03 and varying concentrations of the "anti-idiotype mIgG" in a total volume of 200 ul PBS FA (PBS supplemented with 1% FBS and 0.01% sodium azide) at 4° C. for 30 minutes. After washing 3 times with PBS, 50× diluted FITC-conjugated anti-human FC specific antibody (ImmunoResearch) was added to each tube and incubated at 4° C. for 30 minutes. After repeated washing with PBS (3×), the cells were fixed in 200 µl PBS-FA supplemented with 0.5% formaldehyde. Fixed cells were resuspended in 1 ml PBS and subject to FACScan analysis (Becton Dickenson, Bedford, Mass.). Results indicated that the anti-idiotype antibody effectively inhibits the binding of SM03 to its natural ligand in a dose-dependent manner (FIG. 10).

Example 4

Use of Anti-Idiotype Immunoglobulin to Monitor "the Anti-CD22 Antibodies" in Clinical Trials
"Anti-Idiotype mIgG" from Clone AE6 Binds Specifically to the Antigen-Binding Site (ABS) Sequences Shared by "the Ant-CD22 Antibodies"

The "anti-idiotype mIgG" from clone AE6 binds specifically against the murine, chimeric and humanized form of the anti-CD22 antibody. Using a competitive binding assay, it is further confirmed that the binding epitope of the anti-idiotype antibody resides in the antigen-binding site (ABS) sequences, which are the only sequences shared by murine RFB4, chimeric SM03 and the framework-patched (humanized) SM06. Briefly, 50 µl of 10 µg/ml of the "anti-idiotype mIgG" antibody was added to the wells on ELISA Plate and coating was allowed to proceed overnight at 4° C. Plate was washed 3× with PBS and blocked by 200 µl of 3% BSA in PBS at room temperature for 2 hours, PBS washing was then repeated for 5 times.

SM03 antibodies were conjugated with HRP (SM03-HRP) by TJ Biotechnologies Limited (Tianjin, China). SM03-HRP at 1:4000 dilution was mixed with varying concentrations of competing antibodies, including RFB4, SM03 and SM06, and other irrelevant control antibodies. The mixtures were added into the wells of ELISA plate coated with the "anti-idiotype mIgG". The level of binding of SM03-HRP to the "anti-idiotype mIgG" coated on the ELISA plate after competition was revealed by TMB assays following the manufacturer's specifications (Invitrogen).

Figure 11:
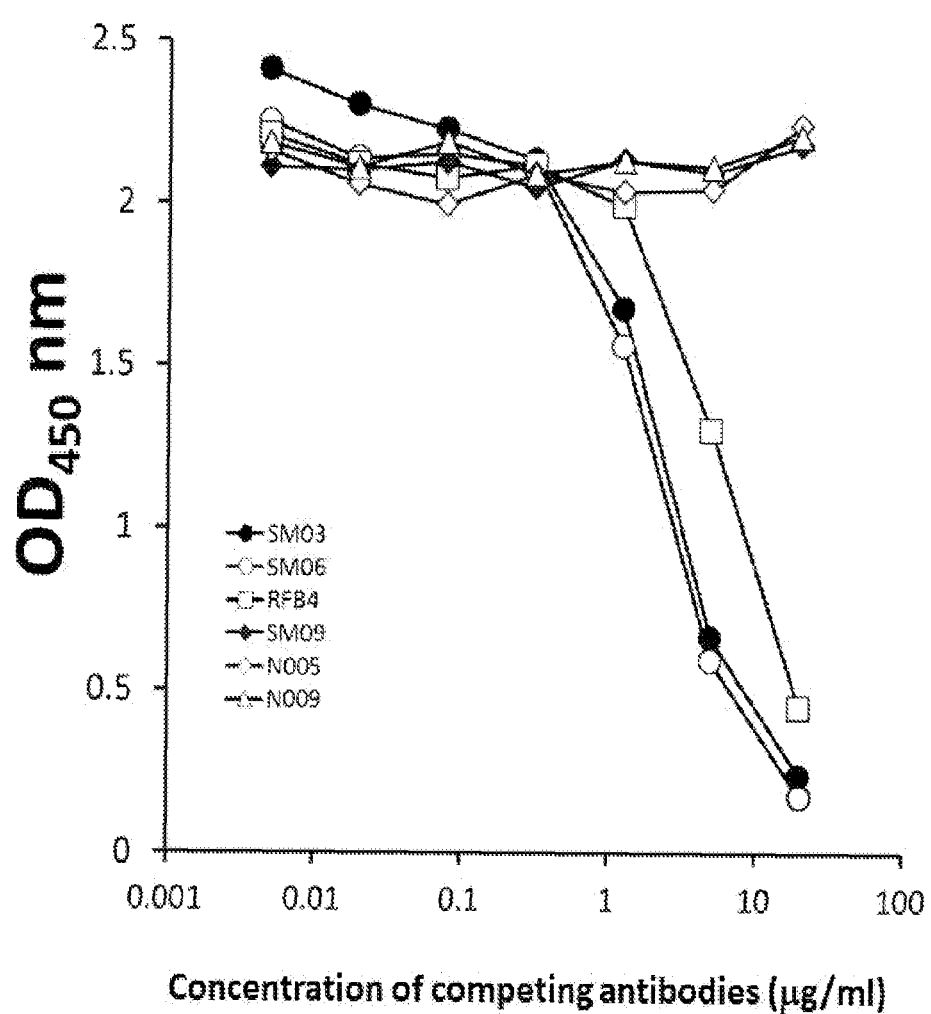
FIG. 11 demonstrates how murine RFB4, chimeric SM03 and framework-patched SM06 can effectively compete with SM03-HRP conjugates for the binding to the "anti-idiotype mIgG."

Results indicated that RFB4, SM03 and SM06 competed equally well with SM03-HRP for the binding to the "anti-idiotype mIgG", while other irrelevant chimeric or humanized antibodies failed to show any competitive binding (FIG. 11), suggesting the "anti-idiotype mIgG" binds specifically to the sequences shared by RFB4, SM03 and SM06, but not by others, i.e. the antigen binding site (ABS).
Use of Murine Anti-SM03 IgG for the Development of a Standard Assay Method to Evaluate the PK of SM03 Clinical Trials With the confirmed specificity of the "anti-idiotype mIgG" against the ABS of "the anti-CD22 antibodies", an ELISA assay can be developed to evaluate the concentration of RFB4, SM03 and SM06 in patient sera during clinical trials. While the example below described the development of an assay to evaluate serum levels of SM03, the method is generally applicable to other members of "anti-CD22 antibodies." Briefly, each well of Microtiter 96-well plates was coated with 0.4 µg/ml of the "anti-idiotype mIgG" in 50 µL PBS, pH 7.4 (4° C., overnight) and was then blocked with 1% BSA for 2 h at room temperature. Serum samples from patients treated with SM03 were diluted with PBS at different concentrations. For the establishment of the standard curve, exogenous SM03 at various known concentrations were diluted with PBS in the presence of normal human serum at a final concentration of 0.1%. 50 µl of serum samples at duplicates were added into the wells of the coated plates, which were subsequently incubated for 2 h at room temperature. HRP-conjugated goat anti-human IgG Fc antibody (1:4000) (Jackson ImmunoResearch) was loaded and incubated for 1 h at room temperature. The reaction was visualized at OD$_{450nm}$ after the addition of 50 µl chromogenic substrate 3,3',5,5'-tetramethylbenzidine (TMB) (Invitrogen); the reaction was stopped after 15 minutes of incubation at RT by the addition of 50 µL 0.18M H$_2$SO$_4$. The concentrations of residual SM03 remaining in the circulation of peripheral blood in patients treated with the therapeutic antibody over time were deduced from a standard curve plot against different known concentrations of exogenous SM03.

Figure 12:
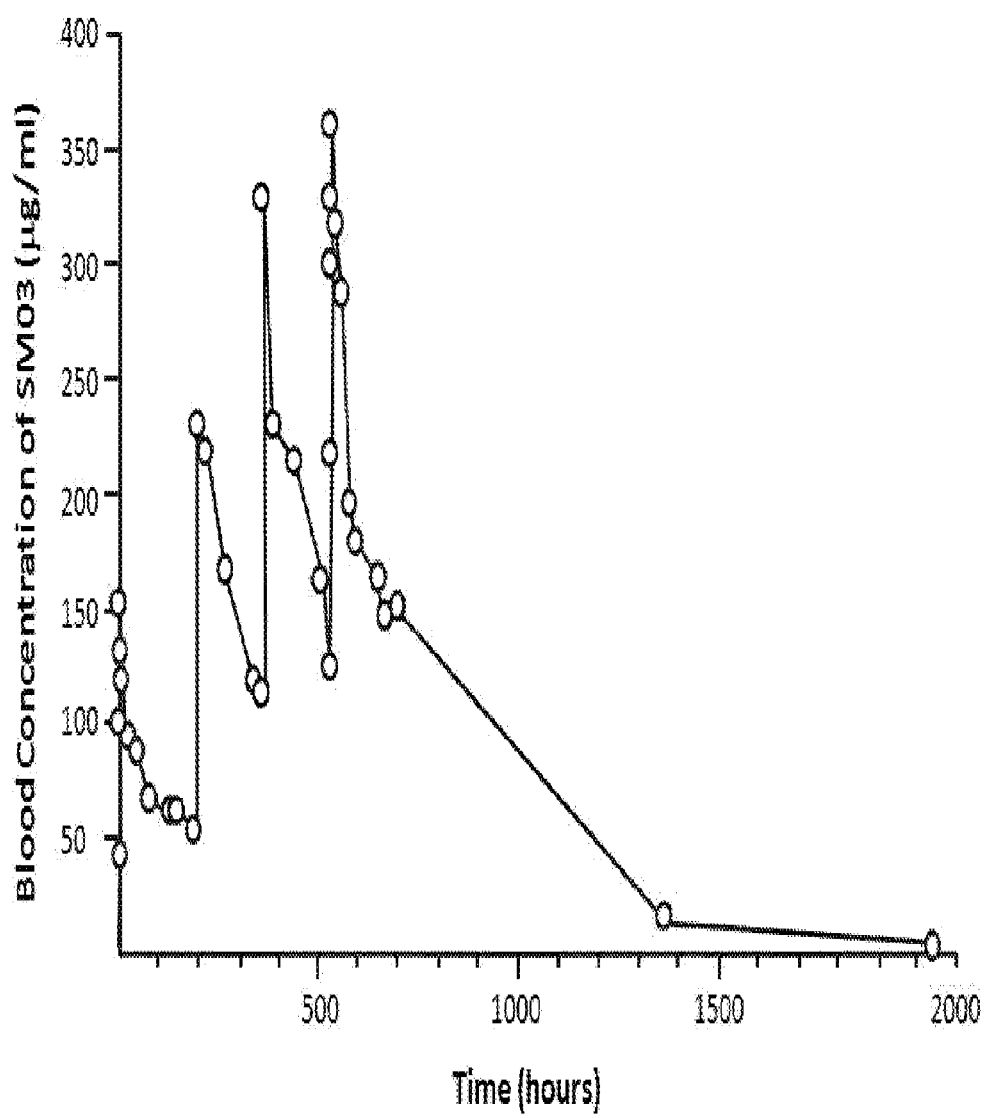
FIG. 12 depicts the pharmacokinetic profile of Lupus patients treated with SM03. The serum concentration of SM03 was determined by ELISA with immobilized "anti-idiotype mIgG" purified from clone AE6 as the capture antibody.

FIG. 12) shows a typical PK profile of a patient treated with SM03, established using the ELISA assay method developed as described above.

Example 5

Novel Approaches for the Evaluation of Biological Activities of Antibodies that Target Internalizing Antigens
Establishment of Cell Lines Expressing the Binding Moiety of the Anti-Idiotype Antibody on the Cell Surface.

In evaluating the activity of therapeutic antibodies, and in the present example, SM03; especially upon storage or during production as a means of quality control, two aspects are considered: binding properties (manifested as affinity and specificity), and the ability of the antibody to induce biological responses (such as ADCC or CDC). The latter is commonly evaluated through bioassays. Since "the anti-CD22 antibodies" bind to human CD22 antigen, which is known to be internalized at a rapid rate (Leung et al. 1995. Construction and characterization of a humanized, internalizing B (CD22)-specific, leukemia/lymphoma antibody, LL2. Mol. Immunol. 32:1413-1427), SM03, as well as other anti-CD22 antibodies, fails to demonstrate the ability to induce CDC reactions in vitro (Liang et al. 2006; Carnahan et al. 2007. Epratuzumab, a CD22-targeting recombinant humanized antibody with a different mode of action from Rituximab. Mol. Immunol. 44:1331-1341). "The anti-CD22 antibodies" bound on the surface of CD22+ cells would not stay on the cell surface long enough to allow the Fc portion of the antigen-bound antibodies to interact with the complement, presumably C1q, for the initiation of a cascade of events leading to cell lyses. That is probably the reason why no measurable CDC activity could be observed with anti-CD22 antibodies such as SM03. The same may be true for other antibodies that target rapidly internalizing surface antigens, such as CD33, Lewis Y antigen, and invariant chains (CD74), etc. Assays that confirm binding properties (specificity and affinity) of the antibody serve to prove the binding moieties formed by the heavy and light chain variable region are properly folded, aligned, and paired together, without information on possible modifications or damages in the Fc region that might result in hampered biological activities in vivo. It is therefore preferable to develop a cell-based assay that can be used for the evaluation of the biological functions of antibodies that target rapidly internalizing antibodies in commonly used bioassays such as CDC or ADCC.

The binding moiety of the anti-idiotype antibody in the present invention is therefore reengineered to allow for expression on the cell surface as a non-internalizing membrane-bound protein. It is done by one of the following ways:
1. Expression of Anti-Idiotype Antibody in the Form of Transmembrane IgD:
    a. Fuse Murine IgD Transmembrane Region Sequence With the CH3 Domain of the "Anti-Idiotype mIgG":
The amino acid sequence of the portion of murine IgD transmembrane (TM) sequence used for fusion to the anti-idiotype mIgG is shown below:

(SEQ ID NO: 17)
GIVNTIQHSCIMDEQSDSYMDLEEENGLWPTMCTFVALFLLTLLYSGFVT
FIKVK.

To construct the gene for the expression of the fusion IgG2a-TM(IgD), a synthetic DNA sequence encoding a portion of the C-terminal end for the "anti-idiotype mIgG" CH3 domain fused to the TM domain of murine IgD was generated. The DNA sequence was flanked by BsrG1 and EagI site to facilitate cloning into the corresponding cloning sites found on the original murine IgG2a constant region. The sequence of the synthetic DNA is shown below (cloning restriction sites underlined). The sequence encodes the last 41 amino acids of the original murine IgG2a fused in frame to the TM(IgD) sequence and is shown below:

(SEQ ID NO: 18)
TGTACAGCAAGCTGAGAGTGGAAAAGAAGAACTGGGTGGAAAGAAATA

GCTACTCCTGTTCAGTGGTCCACGAGGGTCTGCACAATCACCACACGAC

TAAGACCATCTCCCGGTCTCTGGGTAAA-GGCATAGTCAACACCATCCA

ACACTCGTGTATCATGGATGAGCAAAGTGACAGCTACATGGACTTAGAG

GAGGAGAACGGCCTGTGGCCCACAATGTGCACCTTCGTGGCCCTCTTCC

TGCTCACACTGCTCTACAGTGGCTTCGTCACCTTCATCAAGGTGAAGTA

Agtgcga*cggccg*.

The above sequence was cloned into the corresponding cloning sites in the original IgG2a sequence, replacing the C-terminal portion of the IgG2a CH3 domain sequence with a fusion gene containing the same portion of the replaced IgG2a CH3 sequence fused in-frame to the TM sequence of murine IgD. The expressed protein would contain the heavy chain IgG2a immunoglobulin fused to the TM sequence derived from murine IgD immunoglobulin (VH-CH1-hinge-CH2-CH3-TM) (See FIG. 13 and SEQ ID NO: 12).
    b. Replace IgG2a Heavy Chain With Murine IgD Sequence:

The original IgG2a constant region sequence of the "anti-idiotype mIgG" was replaced with that of membrane bound murine IgD. The amino acid sequence of murine IgD with the TM sequence (underlined) is shown below:

(SEQ ID NO: 19)
DKKEPDMFLLSECKAPEENEKINLGCLVIGSQPLKISWEPKKSSIVEHVF

PSEMRNGNYTMVLQVTVLASELNLNHTCTINKPKRKEKPFKFP*ESWDSQS*

*SKRVTPTLQAKNHSTEATKAITTKKDIE*GAMAPSNLTVNILTTSTHPEMS

SWLLCEVSGFFPENIHLMWLGVHSKMKSTNFVTANPTAQPGGTFQTWSVL

RLPVALSSSLDTYTCVVEHEASKTKLNASKSLAIS<u>GIVNTIQHSCIMDEQ</u>

<u>SDSYMDLEEENGLWPTMCTFVALFLLTLLYSGFVTFIKVK</u>.

The DNA sequence encoding the cDNA of the membrane bound form of murine IgD was chemically assembled by standard oligonucleotide synthesis. Cloning restriction sites (XhoI and EagI) were introduced to facilitate cloning into the corresponding sites of the original murine IgG2a expression vector. The sequence of the synthetic DNA is shown (cloning restriction sites underlined). Coding sequence is shown in uppercase, and non-translated sequence in lowercase.

The synthetic sequence is shown below.

(SEQ ID NO: 20)
gccggcaccacctctcttgcagccaacttcactatctgtcttgcaGGTGA

TAAAAAGGAACCTGACATGTTCCTCCTCTCAGAGTGCAAAGCCCCAGAGG

-continued

```
AAAATGAAAAGATAAACCTGGGCTGTTTAGTAATTGGAAGTCAGCCACTG

AAAATCAGCTGGGAGCCAAAGAAGTCAAGTATAGTTGAACATGTCTTCCC

CTCTGAAATGAGAAATGGCAATTATACAATGGTCCTCCAGGTCACTGTGC

TGGCCTCAGAACTGAACCTCAACCACACTTGCACCATAAATAAACCCAAA

AGGAAAGAAAAACCTTTCAAGTTTCCTGAGTCATGGGATTCCCAGTCCTC

TAAGAGAGTCACTCCAACTCTCCAAGCAAAGAATCACTCCACAGAAGCCA

CCAAAGCTATTACCACCAAAAAGGACATAGAAGGGGCCATGGCACCCAGC

AACCTCACTGTGAACATCCTGACCACATCCACCCATCCTGAGATGTCATC

TTGGCTCCTGTGTGAAGTATCTGGCTTCTTCCCGGAAAATATCCACCTCA

TGTGGCTGGGTGTCCACAGTAAAATGAAGTCTACAAACTTTGTCACTGCA

AACCCCACCGCCCAGCCTGGGGGCACATTCCAGACCTGGAGTGTCCTGAG

ACTACCAGTCGCTCTGAGCTCATCACTTGACACTTACACATGTGTGGTGG

AACATGAGGCCTCAAAGACAAAGCTTAATGCCAGCAAGAGCCTAGCAATT

AGTGGCATAGTCAACACCATCCAACACTCGTGTATCATGGATGAGCAAAG

TGACAGCTACATGGACTTAGAGGAGGAGAACGGCCTGTGGCCACAATGT

GCACCTTCGTGGCCCTCTTCCTGCTCACACTGCTCTACAGTGGCTTCGTC

ACCTTCATCAAGGTGAAGTAAgtgcga
```
*cggccg*
```
cgaagcccgctccc cgggctctcgcggtcgcacgaggatgcttggcacgta
```
Ccccc
```
tgtaca
```
.

The above sequence was cloned into the corresponding cloning sites in the original IgG2 expression vector (FIG. 6), replacing the murine IgG2a constant region sequence with that of membrane bound IgD. The expressed protein would contain the heavy chain IgD immunoglobulin with an attached TM sequence (VH-CH1-hinge-CH3-TM). It should be noted that murine IgD lacks the CH2 domain and the structure is very different from that of IgG or human IgD, as shown in FIG. 14 and SEQ ID NO: 13.

For the purpose of illustration, only plasmid DNA for the expression vector for the anti-idiotype IgD-TM as described in (b) above was linearized to establish a transfected cell line. Murine myeloma SP2/0 cells were used as the host cell line for transfection. It is known that SP2/0 produces endogenous Igβ but not Igα (Price et al. 2009. Engineered cell surface expression of membrane immunoglobulin as a means to identify MAb-secreting hybridomas. *J Immunol Methods*. 343:28-41; Wienands et al. 1990. Molecular components of the B cell antigen receptor complex of class IgD differ partly from those of IgM. *EMBO J*. 9:449-455). Since both Igα and Igβ are required in order to bring the IgD immunoglobulin to the cell surface, Igα expression vector (not shown) was co-transfected with the IgD-TM expression vectors into SP2/0 cell using standard electroporation techniques. Cells transfected with the plasmid were selected in the presence of methotrexate conferred by the dihydrofolate reductase (DHFR) gene on the plasmids by standard methods.

Cells surviving selection were tested for surface expression of the anti-idiotype specificity by cell-based ELISA assay. Briefly, 50 μL of SM03 at 10 μg/ml were added to $1\times10^6$ of transfected cells (washed 3× with PBS). The mixture was incubated for 1 h at 4° C., and washed 3× with PBS. 50 μL of HRP-conjugated goat anti-human IgG Fc-specific antibody (Jackson ImmunoResearch) at a dilution of 1:1000 were added into the cells, and were incubated for 1 h at 4° C. Cells were washed once with PBS, and the presence of surface expression of anti-SM03 IgD were revealed by the addition of 50 μL of TMB Solution (Invitrogen). After incubation at RT for 10 min, the reaction was stopped by the addition of 50 μL of 0.18M $H_2SO_4$. Cells were mixed and centrifuged, and supernatant collected for evaluation at $OD_{450}$ nm with an ELISA-plate reader (Sunrise).

Figure 17:
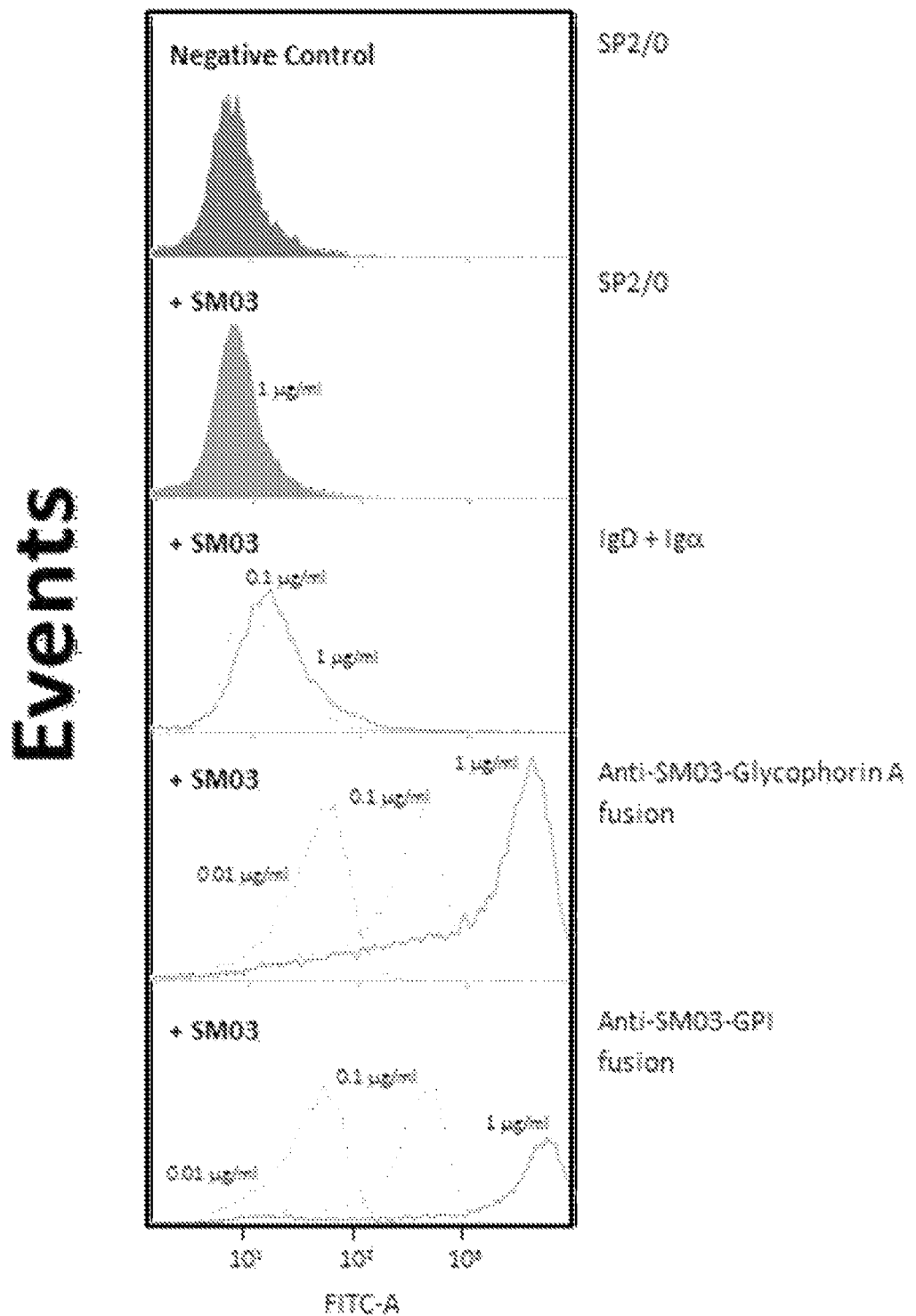
FIG. 17 presents a comparison of surface expression of "anti-idiotype mIgG" in the form of murine IgD, Fab-glycophorin A fusion, and Fab-GPI-fusion proteins on transfectoma cell lines.

Cell clones that demonstrated the highest level of ELISA reading were expanded for further tests (see Table 1 hereinbelow). Results indicated that surface expression of anti-SM03 IgD required the presence of co-transfected Igα in the murine myeloma cells. (Not Shown). Flow cytometry studies confirmed the expression of surface IgD, albeit at a very low level (FIG. 17).

TABLE 1

Cell based ELISA to evaluate surface expression of anti-SM03 IgD (co-transfected with Igα):

| Cell clone | $OD_{450}$ nm | | Surface Expression |
| --- | --- | --- | --- |
| | SM03 + HRP | SM03 + HRP | |
| SP2/0 (negative Control) | 0.088 | 0.273 | − |
| Clone AF9 | 0.144 | 0.329 | − |
| Clone AB4 | 0.141 | 0.428 | − |
| Clone BB4 | 0.177 | 0.501 | − |
| Clone BB5 | 0.165 | 0.572 | − |
| Clone BF9 | 0.143 | 0.459 | − |
| Clone AG5 | 0.151 | 3.076 | +++ |

2. Expression of the "Anti-Idiotype mIgG" Binding Moiety as Cell Surface-Bound Fab-Glycophorin Fusion Protein:

The transmembrane region of Glycophorin A from the red-cell membrane (Terajima et al. 1994. Structural organization of the mouse glycophorin A Gene. J. Biochem 1105-1110; Berg et al. 2002. In Biochemistry 5th Edition. W.H. Freeman & Company, p. 334) was fused to the C-terminal end of the murine IgG2a hinge region of the "anti-idiotype mIgG." The antibody fragment fusion was expected to be expressed on the surface of transfected cells in the form of Fab anchored on the cell surface via the transmembrane region of the Glycophorin A.

The amino acid sequence of the portion of Glycophorin A sequence (including the transmembrane region: boxed) used for fusion to the anti-SM03 antibody fragment is shown below:

(SEQ ID NO: 21)
GERVQLAHHFSEPE ITLIIFGVMAGVIGTILLI SYGIRRLIKKSPSD

VKPLPSPDTDVPLSSVEIENPETSDQ.

The DNA sequence encoding the portion of Glycophorin A sequence (transmembrane region bold and underlined) was codon optimized, and the resultant sequence is shown below:

(SEQ ID NO: 22)
GGCGAGAGGGTGCAGCTGGCCCACCACTTCAGCGAGCCCGAG-

ATCACCCTGATCATCTTCGGCGTGATG

GCCGGCGTGATCGGCACCATCCTGCTGATC-

AGCTACGGCATCAGGAGGCTGATCAAGAAGAGCCCCAGCGACGTGAAGCC

-continued

CCTGCCCAGCCCCGACACCGACGTGCCCCTGAGCAGCGTGGAGATCGAGA

ACCCCGAGACCAGCGACCAGTAA.

The above sequence was fused directly downstream of the sequence encoding the last amino acid of the murine IgG2a hinge region, the expressed protein would contain the heavy chain Fd region of the "anti-idiotype mIgG" fused to the transmembrane and cytoplasmic regions of Glycophorin A protein (VH-CH1-hinge-Glycophorin A transmembrane+cytoplasmic region) (FIG. 15 and SEQ ID NO: 14).

An expression vector for the surface expression of the "anti-idiotype mIgG" Fd fragment—Glycophorin A fusion protein was constructed. Briefly, a DNA sequence encoding portions of the murine IgG2a CH1-hinge region fused to the C-terminal portions (including the transmembrane region sequence) of the Glycophorin A sequence was chemically synthesized by standard oligonucleotide synthesis. The sequence contains in-frame cloning sites XhoI and EagI (underlined). The synthetic sequence was cloned into the corresponding cloning sites of the anti-SM03 IgG2a expression vector (FIG. 6), replacing the CH2-CH3 domain coding sequences of the original IgG2a sequences, using standard techniques in molecular biology. The synthetic sequence is shown below.
Synthetic Sequence (Coding Sequence in Uppercase, Restriction Sites Underlined):

(SEQ ID NO: 23)
CTCGAGCACCTGGCCCAGCCAGTCCATCACCTGCAATGTGGCCCACCCGG

CAAGCAGCACCAAGGTGGACAAGAAAATTGAGCCCAGAGGGCCCACAATC

AAGCCCTGTCCTCCATGCAAATGCCCAGCACCT-GGCGAGAGGGTGCAGC

TGGCCCACCACTTCAGCGAGCCCGAGATCACCCTGATCATCTTCGGCGTG

ATGGCCGGCGTGATCGGCACCATCCTGCTGATCAGCTACGGCATCAGGAG

GCTGATCAAGAAGAGCCCCAGCGACGTGAAGCCCCTGCCCAGCCCCGACA

CCGACGTGCCCCTGAGCAGCGTGGAGATCGAGAACCCCGAGACCAGCGAC

CAGTAAgtgcgacggccggc.

Plasmid DNA for the expression vector for the "anti-idiotype mIgG" Fab-glycophorin A fusion protein was linearized and transfected into mouse SP2/0 cells. Cells transfected with the plasmid were selected in the presence of methotrexate conferred by the dihydrofolate reductase (DHFR) gene on the plasmids by standard methods. Cells surviving selection were tested for surface expression of the anti-idiotype Fab-glycophorin A fusion first by Cell-based ELISA as described above (see Table 2 hereinbelow).

TABLE 2

Cell based ELISA to evaluate surface expression of anti-SM03 Fab'-glycophorin A fusion:

| Cell clone | OD$_{450}$ nm | | Surface Expression |
|---|---|---|---|
| | PBS + HRP | SM03 + HRP | |
| GlycoA clone 1 | 0.45 | 0.579 | – |
| GlycoA clone 3 | 0.498 | 0.406 | – |
| GlycoA clone 5 | 0.309 | 3.532 | +++ |
| GlycoA clone 8 | 0.266 | 0.284 | – |
| GlycoA clone 9 | 0.504 | 0.716 | – |
| GlycoA clone 10 | 0.387 | 0.498 | – |

TABLE 2-continued

Cell based ELISA to evaluate surface expression of anti-SM03 Fab'-glycophorin A fusion:

| Cell clone | OD$_{450}$ nm | | Surface Expression |
|---|---|---|---|
| | PBS + HRP | SM03 + HRP | |
| GlycoA clone 14 | 0.612 | 0.437 | – |
| GlycoA clone 15 | 0.603 | 3.376 | +++ |

Cells demonstrated to have surface expression by ELISA were further analyzed using flow cytometry studies: SM03 was used as the primary antibody, and FITC conjugated goat-anti-human Fc-specific antibody as the detecting (secondary) antibody. Briefly, 5×10$^5$ of the transfected cells were incubated with 1 μg of SM03 in a final volume of 100 μl of PBS supplemented with 1% FCS and 0.01% (w/v) sodium azide (PBS-FA). The mixtures were incubated for 30 minutes at 4° C. and washed three times with PBS to remove unbound antibodies. The binding levels of SM03 to the transfected cells were assessed by the addition of a 20× diluted FITC-labeled, goat anti-human IgG1, Fc fragment-specific antibodies (Jackson ImmunoResearch) in a final volume of 100 μl in PBS-FA, and incubating for 30 minutes at 4° C. The mixture was washed three times with PBS and fluorescence intensities were measured by FACSCAN analysis (Becton Dickinson). Results indicated that anti-idiotype Fab-glycophorin A fusion proteins were effectively expressed on the cell surface of the transfected myeloma cells (FIG. 17).

3. Expression of the "Anti-Idiotype mIgG" Binding Moiety as Fab-GPI Anchor Fusion Protein:

GPI-signal derived from LDL receptor attached to a DAF hydrophobic domain (Moran 1991. J. Cell Biol. 115:1595-1600) was fused downstream of the IgG2a hinge region of the "anti-idiotype mIgG." The fusion protein is expected to be expressed on the surface of transfected cells in the form of Fab attached on the cell surface via the GPI anchor.

The amino acid sequence of the portion of the GPI-signal (boxed) derived from LDL receptor attached to a DAF hydrophobic domain is shown below.

GPI sequence:
(SEQ ID NO: 24)
LTTSGIVTMSHQALG-FTLTGLLGTLVTMGLLT.

The DNA sequence encoding the portion of GPI signal (bold and underlined)—DAF sequence was codon optimized:

(SEQ ID NO: 25)
CTGACCACCAGCGGCATCGTGACCATGAGCCACCAGGCC
CTGGGC-TTCACCCTGACCGGCCTGCTGGGC
ACCCTGGTGACCATGGGCCTGCTGACC.

The above sequence was fused directly downstream of the sequence encoding the last amino acid of the murine IgG2a hinge region; the expressed protein would contain the heavy chain Fd region of the "anti-idiotype mIgG" fused to the GPI-DAF sequence (VH-CH1-GPI-DAF) (FIG. 16 and SEQ ID NO: 15).

An expression vector for the surface expression of the "anti-idiotype mIgG" Fab-GPI-DAF fusion protein was constructed. Briefly, a DNA sequence encoding portions of the murine IgG2a CH1-hinge region fused to the GPI signal- DAF sequence was chemically assembled by standard oligonucleotide synthesis. The sequence contains in-frame cloning sites XhoI and EagI (underlined). The synthetic sequence (shown below). was cloned into the corresponding cloning sites of the "anti-idiotype mIgG" expression vector (FIG. 6), replacing the CH2-CH3 domain coding sequences of the original IgG2a sequences, using standard techniques in molecular biology Synthetic Sequence (Coding Sequence in Uppercase, Restriction Sites Underlined):

(SEQ ID NO: 26)
CTCGAGCACCTGGCCCAGCCAGAGCATCACCTGCAACGTGGCCCACCCCG

CCAGCAGCACCAAGGTGGACAAGAAGATCGAGCCCAGGGGCCCCACCATC

AAGCCCTGCCCCCCCTGCAAGTGCCCCGCCCCCCTGACCACCAGCGGCAT

CGTGACCATGAGCCACCAGGCCCTGGGCTTCACCCTGACCGGCCTGCTGG

GCACCCTGGTGACCATGGGCCTGCTGACCTAAgtgcgacggccg.

Plasmid DNA for the expression vector for the "anti-idiotype mIgG" Fab-GPI-DAF fusion protein was linearized and transfected into mouse SP2/0 cells. Cells transfected with the plasmid are selected in the presence of methotrexate conferred by the dihydrofolate reductase (DHFR) gene on the plasmids by standard methods. Cells surviving selection were tested for surface expression of the "anti-idiotype mIgG" Fab-GPI-DAF fusion first by Cell-based ELISA as described above (see Table 3 hereinbelow).

TABLE 3

Cell based ELISA to evaluate surface expression of anti-SM03 Fab'-GPI-DAF fusion:

| Cell clone | $OD_{450}$ nm | | Surface Expression |
|---|---|---|---|
| | PBS + HRP | SM03 + HRP | |
| GPI clone 1 | 0.588 | 0.623 | – |
| GPI clone 3 | 0.402 | 3.641 | +++ |
| GPI clone 4 | 0.325 | 3.771 | +++ |
| GPI clone 5 | 0.501 | 0.977 | + |
| GPI clone 6 | 0.468 | 0.736 | – |
| GPI clone 7 | 0.467 | 0.7 | – |
| GPI clone 8 | 0.357 | 0.618 | – |
| GPI clone 9 | 0.417 | 0.618 | – |
| GPI clone 10 | 0.636 | 0.85 | – |

Cells demonstrated to have surface expression by ELISA were further analyzed using flow cytometry studies: SM03 was used as the primary antibody, and FITC conjugated goat-anti-human Fc-specific antibody as the detecting (secondary) antibody. Briefly, $5 \times 10^5$ of the transfected cells were incubated with 1 µg of SM03 in a final volume of 100 µl of PBS supplemented with 1% FCS and 0.01% (w/v) sodium azide (PBS-FA). The mixtures were incubated for 30 minutes at 4° C. and washed three times with PBS to remove unbound antibodies. The binding levels of SM03 to the transfected cells were assessed by the addition of a 20× diluted FITC-labeled, goat anti-human IgG1, Fc fragment-specific antibodies (Jackson ImmunoResearch) in a final volume of 100 µl in PBS-FA, and incubating for 30 minutes at 4° C. The mixture was washed three times with PBS and fluorescence intensities were measured by FACSCAN analysis (Becton Dickinson). Cell clones that demonstrated the highest level of fluorescent intensity were expanded for further tests. Results indicated that "anti-idiotype mIgG" Fab-GPI fusion proteins were effectively expressed on the cell surface of the transfected myeloma cells (FIG. 17)

Establishment of a Cell-Based Bioassay for the Evaluation of Biological Activities of "the Anti-CD22 Antibodies"

Figure 18:
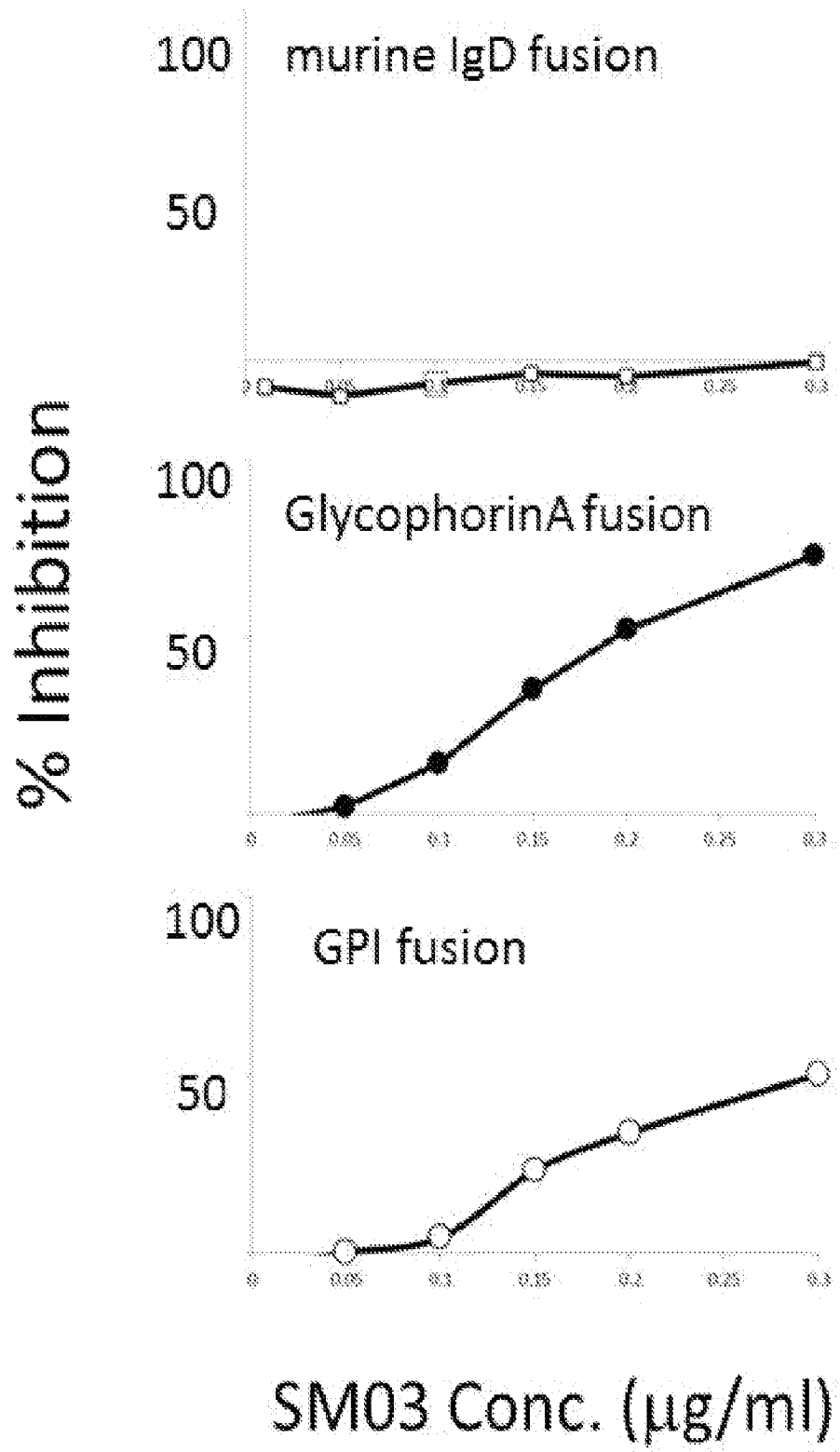
FIG. 18 demonstrates how complement-dependent cytotoxicity (CDC) is induced by SM03 against transfectoma cell lines with surface expression of "anti-idiotype mIgG" in the form of murine IgD, Fab-glycophorin A fusion, and Fab-GPI-fusion proteins.

Transfected cells demonstrated to have surface expression of the anti-idiotype IgD-TM, the "anti-idiotype mIgG" Fab-glycophorin A and Fab-GPI-DAF fusion proteins were adjusted to a density of $2 \times 10^6$/ml. Into each well of a 96-well microtiter-plate, 50 µl of the cells were added. Guinea pig serum (GPS) obtained from Cedarlane (Burlington, Ontario, Canada) in lyophilized form was reconstituted with 1 ml of culture media (100% GPS). 50 µl of SM03 at various concentrations containing 10% GPS were added into wells containing the transfected cells. After incubating at 37° C., 5% $CO_2$, for 2 h, 20 µl of CCK-8 (cell counting kit-8) reagent (Dojindo Molecular Technologies, Rockville, Md.), were added into each well. Cell viabilities were determined at OD450 three h later, according to the manufacturer's specification. Results indicated that "the anti-CD22 antibodies" such as SM03 effectively directed complement dependent cell cytotoxicity (CDC) against the cell lines with demonstrated surface expression of the "anti-idiotype mIgG" Fab-glycophorin A fusion and Fab-GPI-DAF fusion protein (FIG. 18). No appreciable CDC was observed with cell line expressing surface anti-idiotype IgD-TM. Either the surface IgD tends to internalize upon binding to "the anti-CD22 antibodies" (Geisberger et al. 2006. Membrane IgM influences membrane IgD mediated antigen internalization in the B cell line Bcl1. Immunol. Letters 102:169-176), rendering CDC unlikely, or the cell surface density of the expressed anti-idiotype IgD-TM not reaching the required threshold for the initiation of complement activation. Regardless, at least two of the three cell lines with surface expression of the binding moiety of the "anti-idiotype mIgG" were effective in inducing CDC killings mediated by SM03 in a dose-dependent manner, demonstrating that the approaches can be used as a general method for the development of bioassays suitable for evaluating the functionality of antibodies that bind to internalizing surface antigens.

All patents, patent applications, and publications cited herein are incorporated by reference in their entirety.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is defined not by the above description, but by the following claims and their equivalents.

What is claimed:

1. A method of generating a surrogate target cell line that expresses at its surface a binding moiety of an anti-idiotype antibody or derivative thereof that specifically binds an epitope on an anti-CD22 monoclonal antibody that is shared by murine RFB4, chimeric SM03, and framework-patched SM06, wherein said anti-idiotype antibody or derivative thereof includes the following heavy chain variable region sequences: CDR-1 (SEQ ID NO:1), CDR-2 (SEQ ID NO:2), and CDR-3 (SEQ ID NO:3), and the following light chain variable region sequences: CDR1 (SEQ ID NO:4), CDR2 (SEQ ID NO:5), and CDR3 (SEQ ID NO:6), said method comprising the steps of:
  a. genetically fusing the binding moiety of said anti-idiotypic antibody with a cell surface membrane anchoring moiety to give rise to an anti-idiotypic fusion protein, wherein said cell surface membrane anchoring moiety is selected from the group consisting of:
    i. a transmembrane portion of a membrane bound IgD protein;
    ii. a transmembrane portion of a membrane bound glycophorin A protein; and
    iii. a glycophosphatidylinositol (GPI) signal sequence;
  b. transfecting a mammalian cell line with said anti-idiotypic fusion protein; and
  c. culturing said mammalian cell line so as to effectuate the expression of said anti-idiotypic fusion protein at the surface of said a mammalian cell.

2. The method of claim 1, wherein said anti-idiotypic antibody or derivative thereof is in the form of an scFv, an Fab, an Fab' or an F(ab')₂.

3. The method of claim 1, further wherein said anti-idiotype antibody takes the form of a whole IgG murine IgG2a/kappa isotype or another human or non-human isotype and said derivative is selected from the group consisting of an F(ab')₂, Fab, Fab', Fd, Fabc, scFv, diabody, bispecific antibody, and antibody conjugate.

4. The method of claim 3, wherein said cell surface membrane anchoring moiety is selected from the group consisting of a transmembrane region of mouse or human glycophorin A protein, a transmembrane region of mouse or human IgD, and a glycophosphatidylinositol (GPI) signal sequence of a decay accelerating factor (DAF) protein.

5. The method of claim 1, wherein said cell surface membrane anchoring moiety comprises the transmembrane region of mouse or human glycophorin A protein.

6. The method of claim 5, wherein said transmembrane region of mouse or human glycophorin A protein comprises amino acids 15 to 33 of SEQ ID NO: 21.

7. The method of claim 5, wherein said cell surface membrane anchoring moiety comprises SEQ ID NO: 21.

8. The method of claim 1, wherein said cell surface membrane anchoring moiety comprises the transmembrane region of mouse or human IgD.

9. The method of claim 8, wherein said cell surface membrane anchoring moiety comprises SEQ ID NO:17.

10. The method of claim 1, wherein said cell surface membrane anchoring moiety comprises a glycophosphatidylinositol (GPI) signal sequence of a decay accelerating factor (DAF) protein.

11. The method of claim 10, wherein said GPI signal sequence comprises amino acids 1 to 15 of SEQ ID NO: 24.

12. The method of claim 11, wherein said cell surface membrane anchoring moiety is encoded by SEQ ID NO: 25.

13. The method of claim 12, wherein said cell surface membrane anchoring moiety comprises SEQ ID NO: 24.

14. The method of claim 1, wherein said epitope on said an anti-CD22 monoclonal antibody comprises an antigen-binding site specific to CD22.

* * * * *

SEQUENCE LISTING

<160> NUMBER OF SEQ ID NOS: 26

<210> SEQ ID NO 1
<211> LENGTH: 5

```
<212> TYPE: PRT
<213> ORGANISM: Artificial Sequence
<220> FEATURE:
<223> OTHER INFORMATION: CDR-1 heavy chain variable sequence from scFv
      phage #1

<400> SEQUENCE: 1

Asn Tyr Val Thr His
1               5

<210> SEQ ID NO 2
<211> LENGTH: 17
<212> TYPE: PRT
<213> ORGANISM: Artificial Sequence
<220> FEATURE:
<223> OTHER INFORMATION: CDR-2 heavy chain variable sequence for scFv
      phage #2

<400> SEQUENCE: 2

Tyr Ile Asn Pro Tyr Ser Asp Gly Ser Lys Tyr Asn Glu Lys Phe Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: CDR-3 heavy chain variable sequence for scFv
      phage #3

<400> SEQUENCE: 3

Gly Lys Thr Glu Trp Phe Pro Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: CDR-1 light chain variable sequence for scFv
      phage #1

<400> SEQUENCE: 4

Lys Ala Ser Gln Ser Val Asp Tyr Asp Gly Asp Ser Tyr Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR-2 light chain variable sequence for scFv
      phage #2

<400> SEQUENCE: 5

Ala Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR-3 light chain variable sequence for scFv
      phage #3
<220> FEATURE:
<221> NAME/KEY: MISC_FEATURE
```

```
<222> LOCATION: (8)..(8)
<223> OTHER INFORMATION: X may be F or Y

<400> SEQUENCE: 6

Gln Gln Ser Asn Lys Asp Pro Xaa Thr
1               5

<210> SEQ ID NO 7
<211> LENGTH: 240
<212> TYPE: PRT
<213> ORGANISM: Artificial Sequence
<220> FEATURE:
<223> OTHER INFORMATION: scFv for phage #3

<400> SEQUENCE: 7

Gln Val Gln Leu Val Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
                20                  25                  30

Val Thr His Trp Val Lys Gln Lys Pro Gly Gln Gly Leu Glu Trp Ile
            35                  40                  45

Gly Tyr Ile Asn Pro Tyr Ser Asp Gly Ser Lys Tyr Asn Glu Lys Phe
    50                  55                  60

Lys Gly Lys Ala Thr Leu Thr Ser Asp Glu Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Gly Lys Thr Glu Trp Phe Pro Tyr Trp Gly Gln Gly Thr Pro
            100                 105                 110

Leu Thr Val Ser Gly Gly Gly Ser Gly Ser Gly Ser Ser Gly Gly
        115                 120                 125

Gly Gly Asp Ile Val Leu Thr Gln Thr Pro Ala Ser Leu Ala Val Ser
    130                 135                 140

Leu Gly Gln Arg Ala Thr Ile Ser Cys Lys Ala Ser Gln Ser Val Asp
145                 150                 155                 160

Tyr Asp Gly Asp Ser Tyr Met Asn Trp Tyr Gln Gln Lys Pro Gly Gln
                165                 170                 175

Pro Pro Lys Leu Leu Ile Tyr Ala Ala Ser Asn Leu Glu Ser Gly Ile
            180                 185                 190

Pro Ala Arg Phe Ser Gly Ser Gly Ser Gly Thr Asp Phe Thr Leu Asn
        195                 200                 205

Ile His Pro Val Glu Glu Glu Asp Ala Ala Thr Tyr Tyr Cys Gln Gln
    210                 215                 220

Ser Asn Glu Asp Pro Phe Thr Phe Gly Gly Gly Thr Lys Leu Glu Ile
225                 230                 235                 240

<210> SEQ ID NO 8
<211> LENGTH: 1344
<212> TYPE: DNA
<213> ORGANISM: Artificial Sequence
<220> FEATURE:
<223> OTHER INFORMATION: heavy chain of the anti-idiotype mIgG expressed
      in clone AE6

<400> SEQUENCE: 8
caggtccaac tgcagcagtc tggacctgag ctggtaaagc ctggggcttc agtgaagatg      60
tcctgcaagg cttctggata cacattcact aactatgtta cgcactgggt gaagcagaag     120
cctgggcagg gccttgagtg gattggatat attaatcctt acagtgatgg ttctaagtac     180
```

```
aatgagaagt tcaaaggcaa ggccacactg acttcagacg aatcctccag cacagcctac    240
atggagctca gcagcctgac ctctgaggac tctgcggtct attactgtgc aagagggaaa    300
accgagtggt ttccttactg gggtcaaggc actacggtca ccgtctcctc agccaaaaca    360
acagccccat cggtctatcc actggcccct gtgtgtggag atacaactgg ctcttcggtg    420
actctaggat gcctggtcaa gggttatttc cctgagccag tgaccttgac ctggaactct    480
ggatccctgt ccagtggtgt gcacaccttc ccagctgtcc tgcagtctga cctctacacc    540
ctcagcagct cagtgactgt aacctcgagc acctggccca gccagtccat cacctgcaat    600
gtggcccacc cggcaagcag caccaaggtg gacaagaaaa ttgagcccag agggcccaca    660
atcaagccct gtcctccatg caaatgccca gcacctaacc tcttgggtgg accatccgtc    720
ttcatcttcc ctccaaagat caaggatgta ctcatgatct ccctgagccc catagtcaca    780
tgtgtggtgg tggatgtgag cgaggatgac ccagatgtcc agatcagctg gtttgtgaac    840
aacgtggaag tacacacagc tcagacacaa acccatagag aggattacaa cagtactctc    900
cgggtggtca gtgccctccc catccagcac caggactgga tgagtggcaa ggagttcaaa    960
tgcaaggtca acaacaaaga cctcccagcg cccatcgaga gaaccatctc aaaacccaaa   1020
gggtcagtaa gagctccaca ggtatatgtc ttgcctccac cagaagaaga gatgactaag   1080
aaacaggtca ctctgacctg catggtcaca gacttcatgc ctgaagacat ttacgtggag   1140
tggaccaaca acgggaaaac agagctaaac tacaagaaca ctgaaccagt cctggactct   1200
gatggttctt acttcatgta cagcaagctg agagtggaaa agaagaactg ggtggaaaga   1260
aatagctact cctgttcagt ggtccacgag ggtctgcaca tcaccttcac gactaagacc   1320
atctcccggt ctctgggtaa ataa                                          1344
```

<210> SEQ ID NO 9  
<211> LENGTH: 447  
<212> TYPE: PRT  
<213> ORGANISM: Artificial Sequence  
<220> FEATURE:  
<223> OTHER INFORMATION: translated heavy chain of the anti-idiotype mIgG expressed in clone AE6

<400> SEQUENCE: 9

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Thr His Trp Val Lys Gln Lys Pro Gly Gln Gly Leu Glu Trp Ile
        35                  40                  45

Gly Tyr Ile Asn Pro Tyr Ser Asp Gly Ser Lys Tyr Asn Glu Lys Phe
    50                  55                  60

Lys Gly Lys Ala Thr Leu Thr Ser Asp Glu Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Lys Thr Glu Trp Phe Pro Tyr Trp Gly Gln Gly Thr Thr
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140
```

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
            165                 170                 175

Asp Leu Tyr Thr Leu Ser Ser Ser Val Thr Val Thr Ser Ser Thr Trp
                180                 185                 190

Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
                260                 265                 270

Val Gln Ile Ser Trp Phe Val Asn Asn Val Glu Val His Thr Ala Gln
            275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His Leu Thr Thr Lys Thr Ile Ser Arg Ser Leu Gly Lys
            435                 440                 445

<210> SEQ ID NO 10
<211> LENGTH: 660
<212> TYPE: DNA
<213> ORGANISM: Artificial Sequence
<220> FEATURE:
<223> OTHER INFORMATION: light chain of the anti-idiotype mIgG expressed
      in clone AE6

<400> SEQUENCE: 10
gatattgttc tcacccagac tccagcttct ttggctgtgt ctctagggca gagggccacc      60
atctcctgca aggccagcca aagtgttgat tatgatggtg atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtaatga ggatccattc     300
acgttcggag gtgggacaaa attggaaata aaacgacggg ctgatgctgc accaactgta     360

```
tccatcttcc caccatccag tgagcagtta acatctggag gtgcctcagt cgtgtgcttc    420
ttgaacaact tctaccccaa agacatcaat gtcaagtgga agattgatgg cagtgaacga    480
caaaatggcg tcctgaacag ttggactgat caggacagca agacagcac ctacagcatg     540 agcagcaccc tcacgttgac caaggacgag tatgaacgac ataacagcta ycctgtgag     600 gccactcaca agacatcaac ttcacccatt gtcaagagct caacaggaa tgagtgttaa     660
```

<210> SEQ ID NO 11
<211> LENGTH: 219
<212> TYPE: PRT
<213> ORGANISM: Artificial Sequence
<220> FEATURE:
<223> OTHER INFORMATION: translated light chain of the anti-idiotype mIgG expressed in clone AE6

<400> SEQUENCE: 11

```
Asp Ile Val Leu Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Gly Gly Thr Lys Leu Glu Ile Lys Arg
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 12
<211> LENGTH: 502
<212> TYPE: PRT
<213> ORGANISM: Artificial Sequence
<220> FEATURE:
<223> OTHER INFORMATION: murine IgD transmembrane region fused with the CH3 domain of anti-idiotype mIgG

<400> SEQUENCE: 12

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
```

```
                20                  25                  30
Val Thr His Trp Val Lys Gln Lys Pro Gly Gln Gly Leu Glu Trp Ile
                35                  40                  45
Gly Tyr Ile Asn Pro Tyr Ser Asp Gly Ser Lys Tyr Asn Glu Lys Phe
            50                  55                  60
Lys Gly Lys Ala Thr Leu Thr Ser Asp Glu Ser Ser Thr Ala Tyr
65                  70                  75                  80
Met Glu Leu Ser Ser Leu Thr Ser Glu Asp Ser Ala Val Tyr Tyr Cys
                85                  90                  95
Ala Arg Gly Lys Thr Glu Trp Phe Pro Tyr Trp Gly Gln Gly Thr Thr
                100                 105                 110
Val Thr Val Ser Ser Ala Lys Thr Thr Ala Pro Ser Val Tyr Pro Leu
            115                 120                 125
Ala Pro Val Cys Gly Asp Thr Thr Gly Ser Ser Val Thr Leu Gly Cys
            130                 135                 140
Leu Val Lys Gly Tyr Phe Pro Glu Pro Val Thr Leu Thr Trp Asn Ser
145                 150                 155                 160
Gly Ser Leu Ser Ser Gly Val His Thr Phe Pro Ala Val Leu Gln Ser
                165                 170                 175
Asp Leu Tyr Thr Leu Ser Ser Ser Val Thr Val Thr Ser Ser Thr Trp
                180                 185                 190
Pro Ser Gln Ser Ile Thr Cys Asn Val Ala His Pro Ala Ser Ser Thr
            195                 200                 205
Lys Val Asp Lys Lys Ile Glu Pro Arg Gly Pro Thr Ile Lys Pro Cys
            210                 215                 220
Pro Pro Cys Lys Cys Pro Ala Pro Asn Leu Leu Gly Gly Pro Ser Val
225                 230                 235                 240
Phe Ile Phe Pro Pro Lys Ile Lys Asp Val Leu Met Ile Ser Leu Ser
                245                 250                 255
Pro Ile Val Thr Cys Val Val Asp Val Ser Glu Asp Asp Pro Asp
            260                 265                 270
Val Gln Ile Ser Trp Phe Val Asn Asn Val Glu Val His Thr Ala Gln
            275                 280                 285
Thr Gln Thr His Arg Glu Asp Tyr Asn Ser Thr Leu Arg Val Val Ser
            290                 295                 300
Ala Leu Pro Ile Gln His Gln Asp Trp Met Ser Gly Lys Glu Phe Lys
305                 310                 315                 320
Cys Lys Val Asn Asn Lys Asp Leu Pro Ala Pro Ile Glu Arg Thr Ile
                325                 330                 335
Ser Lys Pro Lys Gly Ser Val Arg Ala Pro Gln Val Tyr Val Leu Pro
            340                 345                 350
Pro Pro Glu Glu Glu Met Thr Lys Lys Gln Val Thr Leu Thr Cys Met
            355                 360                 365
Val Thr Asp Phe Met Pro Glu Asp Ile Tyr Val Glu Trp Thr Asn Asn
            370                 375                 380
Gly Lys Thr Glu Leu Asn Tyr Lys Asn Thr Glu Pro Val Leu Asp Ser
385                 390                 395                 400
Asp Gly Ser Tyr Phe Met Tyr Ser Lys Leu Arg Val Glu Lys Lys Asn
                405                 410                 415
Trp Val Glu Arg Asn Ser Tyr Ser Cys Ser Val Val His Glu Gly Leu
            420                 425                 430
His Asn His Leu Thr Thr Lys Thr Ile Ser Arg Ser Leu Gly Lys Gly
            435                 440                 445
```

```
Ile Val Asn Thr Ile Gln His Ser Cys Ile Met Asp Glu Gln Ser Asp
    450                 455                 460
Ser Tyr Met Asp Leu Glu Glu Asn Gly Leu Trp Pro Thr Met Cys
465                 470                 475                 480
Thr Phe Val Ala Leu Phe Leu Leu Thr Leu Leu Tyr Ser Gly Phe Val
                485                 490                 495
Thr Phe Ile Lys Val Lys
            500

<210> SEQ ID NO 13
<211> LENGTH: 408
<212> TYPE: PRT
<213> ORGANISM: Artificial Sequence
<220> FEATURE:
<223> OTHER INFORMATION: anti-idiotype mIgG with membrane bound murine
      IgD

<400> SEQUENCE: 13

Gln Val Gln Leu Gln Gln Ser Gly Pro Glu Leu Val Lys Pro Gly Ala
1               5                   10                  15
Ser Val Lys Met Ser Cys Lys Ala Ser Gly Tyr Thr Phe Thr Asn Tyr
            20                  25                  30
Val Thr His Trp Val Lys Gln Lys Pro Gly Gln Gly Leu Glu Trp Ile
        35                  40                  45
Gly Tyr Ile Asn Pro Tyr Ser Asp Gly Ser Lys Tyr Asn Glu Lys Phe
    50                  55                  60
Lys Gly Lys Ala Thr Leu Thr Ser Asp Glu Ser Ser Ser Thr Ala Tyr
65                  70                  75                  80
Met Glu Leu Ser Ser Leu Thr Ser Glu Asp Ser Ala Val Tyr Tyr Cys
                85                  90                  95
Ala Arg Gly Lys Thr Glu Trp Phe Pro Tyr Trp Gly Gln Gly Thr Thr
            100                 105                 110
Val Thr Val Ser Ser Gly Asp Lys Lys Glu Pro Asp Met Phe Leu Leu
        115                 120                 125
Ser Glu Cys Lys Ala Pro Glu Glu Asn Glu Lys Ile Asn Leu Gly Cys
    130                 135                 140
Leu Val Ile Gly Ser Gln Pro Leu Lys Ile Ser Trp Glu Pro Lys Lys
145                 150                 155                 160
Ser Ser Ile Val Glu His Val Phe Pro Ser Glu Met Arg Asn Gly Asn
                165                 170                 175
Tyr Thr Met Val Leu Gln Val Thr Val Leu Ala Ser Glu Leu Asn Leu
            180                 185                 190
Asn His Thr Cys Thr Ile Asn Lys Pro Lys Arg Lys Glu Lys Pro Phe
        195                 200                 205
Lys Phe Pro Glu Ser Trp Asp Ser Gln Ser Ser Lys Arg Val Thr Pro
    210                 215                 220
Thr Leu Gln Ala Lys Asn His Ser Thr Glu Ala Thr Lys Ala Ile Thr
225                 230                 235                 240
Thr Lys Lys Asp Ile Glu Gly Ala Met Ala Pro Ser Asn Leu Thr Val
                245                 250                 255
Asn Ile Leu Thr Thr Ser Thr His Pro Glu Met Ser Ser Trp Leu Leu
            260                 265                 270
Cys Glu Val Ser Gly Phe Phe Pro Glu Asn Ile His Leu Met Trp Leu
        275                 280                 285
Gly Val His Ser Lys Met Lys Ser Thr Asn Phe Val Thr Ala Asn Pro
```

```
            290                 295                 300
Thr Ala Gln Pro Gly Gly Thr Phe Gln Thr Trp Ser Val Leu Arg Leu
305                 310                 315                 320

Pro Val Ala Leu Ser Ser Leu Asp Thr Tyr Thr Cys Val Val Glu
                325                 330                 335

His Glu Ala Ser Lys Thr Lys Leu Asn Ala Ser Lys Ser Leu Ala Ile
                340                 345                 350

Ser Gly Ile Val Asn Thr Ile Gln His Ser Cys Ile Met Asp Glu Gln
                355                 360                 365

Ser Asp Ser Tyr Met Asp Leu Glu Glu Glu Asn Gly Leu Trp Pro Thr
                370                 375                 380

Met Cys Thr Phe Val Ala Leu Phe Leu Leu Thr Leu Leu Tyr Ser Gly
385                 390                 395                 400

Phe Val Thr Phe Ile Lys Val Lys
                405
```

<210> SEQ ID NO 14
<211> LENGTH: 305
<212> TYPE: PRT
<213> ORGANISM: Artificial Sequence
<220> FEATURE:
<223> OTHER INFORMATION: heavy chain Fd region of the anti-idiotype mIgG
      fused to the transmembrane and cytoplasmic regions of Glycophorin
      A protein

<400> SEQUENCE: 14

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
                20                  25                  30

Val Thr His Trp Val Lys Gln Lys Pro Gly Gln Gly Leu Glu Trp Ile
                35                  40                  45

Gly Tyr Ile Asn Pro Tyr Ser Asp Gly Ser Lys Tyr Asn Glu Lys Phe
            50                  55                  60

Lys Gly Lys Ala Thr Leu Thr Ser Asp Glu Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Lys Thr Glu Trp Phe Pro Tyr Trp Gly Gln Gly Thr Thr
                100                 105                 110

Val Thr Val Ser Ser Ala Lys Thr Thr Ala Pro Ser Val Tyr Pro Leu
                115                 120                 125

Ala Pro Val Cys Gly Asp Thr Thr Gly Ser Ser Val Thr Leu Gly Cys
            130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
                180                 185                 190

Pro Ser Gln Ser Ile Thr Cys Asn Val Ala His Pro Ala Ser Ser Thr
                195                 200                 205

Lys Val Asp Lys Lys Ile Glu Pro Arg Gly Pro Thr Ile Lys Pro Cys
            210                 215                 220

Pro Pro Cys Lys Cys Pro Ala Pro Gly Glu Arg Val Gln Leu Ala His
225                 230                 235                 240
```

His Phe Ser Glu Pro Glu Ile Thr Leu Ile Ile Phe Gly Val Met Ala
                245                 250                 255

Gly Val Ile Gly Thr Ile Leu Leu Ile Ser Tyr Gly Ile Arg Arg Leu
            260                 265                 270

Ile Lys Lys Ser Pro Ser Asp Val Lys Pro Leu Pro Ser Pro Asp Thr
        275                 280                 285

Asp Val Pro Leu Ser Ser Val Glu Ile Glu Asn Pro Glu Thr Ser Asp
    290                 295                 300

Gln
305

<210> SEQ ID NO 15
<211> LENGTH: 264
<212> TYPE: PRT
<213> ORGANISM: Artificial Sequence
<220> FEATURE:
<223> OTHER INFORMATION: heavy chain Fd region of the anti-idiotype mIgG
      fused to the GPI-DAF sequence

<400> SEQUENCE: 15

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Thr His Trp Val Lys Gln Lys Pro Gly Gln Gly Leu Glu Trp Ile
        35                  40                  45

Gly Tyr Ile Asn Pro Tyr Ser Asp Gly Ser Lys Tyr Asn Glu Lys Phe
    50                  55                  60

Lys Gly Lys Ala Thr Leu Thr Ser Asp Glu Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Lys Thr Glu Trp Phe Pro Tyr Trp Gly Gln Gly Thr Thr
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Leu Thr Thr Ser Gly Ile Val Thr
225                 230                 235                 240

Met Ser His Gln Ala Leu Gly Phe Thr Leu Thr Gly Leu Leu Gly Thr
                245                 250                 255

Leu Val Thr Met Gly Leu Leu Thr
            260

-continued

```
<210> SEQ ID NO 16
<211> LENGTH: 14
<212> TYPE: PRT
<213> ORGANISM: Artificial Sequence
<220> FEATURE:
<223> OTHER INFORMATION: scFv linker sequence

<400> SEQUENCE: 16

Gly Gly Gly Gly Ser Gly Ser Gly Ser Ser Gly Gly Gly Gly
1               5                   10

<210> SEQ ID NO 17
<211> LENGTH: 55
<212> TYPE: PRT
<213> ORGANISM: Artificial Sequence
<220> FEATURE:
<223> OTHER INFORMATION: portion of the murine IgD transmembrane (TM)
      sequence used for fusion to the anti-idiotype mIgG

<400> SEQUENCE: 17

Gly Ile Val Asn Thr Ile Gln His Ser Cys Ile Met Asp Glu Gln Ser
1               5                   10                  15

Asp Ser Tyr Met Asp Leu Glu Glu Glu Asn Gly Leu Trp Pro Thr Met
            20                  25                  30

Cys Thr Phe Val Ala Leu Phe Leu Leu Thr Leu Leu Tyr Ser Gly Phe
        35                  40                  45

Val Thr Phe Ile Lys Val Lys
    50                  55

<210> SEQ ID NO 18
<211> LENGTH: 305
<212> TYPE: DNA
<213> ORGANISM: Artificial Sequence
<220> FEATURE:
<223> OTHER INFORMATION: Synthetic DNA sequence encoding a portion of
      the C-terminal end of the anti-idiotype mIgG CH3 domain fused to
      the TM domain of murine IgD

<400> SEQUENCE: 18
tgtacagcaa gctgagagtg aaaagaaga actgggtgga agaaatagc tactcctgtt      60 cagtggtcca cgagggtctg cacaatcacc acacgactaa gaccatctcc cggtctctgg   120
gtaaaggcat agtcaacacc atccaacact cgtgtatcat ggatgagcaa agtgacagct   180
acatggactt agaggaggag aacggcctgt ggcccacaat gtgcaccttc gtggccctct   240
tcctgctcac actgctctac agtggcttcg tcaccttcat caaggtgaag taagtgcgac   300
ggccg                                                              305

<210> SEQ ID NO 19
<211> LENGTH: 290
<212> TYPE: PRT
<213> ORGANISM: Artificial Sequence
<220> FEATURE:
<223> OTHER INFORMATION: murine IgD with the transmembrane (TM) sequence

<400> SEQUENCE: 19

Asp Lys Lys Glu Pro Asp Met Phe Leu Leu Ser Glu Cys Lys Ala Pro
1               5                   10                  15

Glu Glu Asn Glu Lys Ile Asn Leu Gly Cys Leu Val Ile Gly Ser Gln
            20                  25                  30

Pro Leu Lys Ile Ser Trp Glu Pro Lys Lys Ser Ser Ile Val Glu His
        35                  40                  45

Val Phe Pro Ser Glu Met Arg Asn Gly Asn Tyr Thr Met Val Leu Gln
```

```
            50                  55                  60
Val Thr Val Leu Ala Ser Glu Leu Asn Leu Asn His Thr Cys Thr Ile
 65                  70                  75                  80

Asn Lys Pro Lys Arg Lys Glu Lys Pro Phe Lys Phe Pro Glu Ser Trp
                 85                  90                  95

Asp Ser Gln Ser Ser Lys Arg Val Thr Pro Thr Leu Gln Ala Lys Asn
            100                 105                 110

His Ser Thr Glu Ala Thr Lys Ala Ile Thr Thr Lys Lys Asp Ile Glu
        115                 120                 125

Gly Ala Met Ala Pro Ser Asn Leu Thr Val Asn Ile Leu Thr Thr Ser
    130                 135                 140

Thr His Pro Glu Met Ser Ser Trp Leu Leu Cys Glu Val Ser Gly Phe
145                 150                 155                 160

Phe Pro Glu Asn Ile His Leu Met Trp Leu Gly Val His Ser Lys Met
                165                 170                 175

Lys Ser Thr Asn Phe Val Thr Ala Asn Pro Thr Ala Gln Pro Gly Gly
            180                 185                 190

Thr Phe Gln Thr Trp Ser Val Leu Arg Leu Pro Val Ala Leu Ser Ser
        195                 200                 205

Ser Leu Asp Thr Tyr Thr Cys Val Val Glu His Glu Ala Ser Lys Thr
    210                 215                 220

Lys Leu Asn Ala Ser Lys Ser Leu Ala Ile Ser Gly Ile Val Asn Thr
225                 230                 235                 240

Ile Gln His Ser Cys Ile Met Asp Gly Gln Ser Asp Ser Tyr Met Asp
                245                 250                 255

Leu Glu Glu Glu Asn Gly Leu Trp Pro Thr Met Cys Thr Phe Val Ala
            260                 265                 270

Leu Phe Leu Leu Thr Leu Leu Tyr Ser Gly Phe Val Thr Phe Ile Lys
        275                 280                 285

Val Lys
    290

<210> SEQ ID NO 20
<211> LENGTH: 334
<212> TYPE: DNA
<213> ORGANISM: Artificial Sequence
<220> FEATURE:
<223> OTHER INFORMATION: coding sequence for membrane bound form of
      murine IgD

<400> SEQUENCE: 20
gccggcacca cctctcttgc agccaacttc actatctgtc ttgcaggtga taaaaggaa      60 cctgacatgt tcctcctctc agagtgcaaa gccccagagg aaaatgaaaa gataaacctg   120
ggctgtttag taattggaag tcagccactg aaaatcagct gggagccaaa gaagtcaagt   180
atagttgaac atgtcttccc ctctgaaatg agaaatggca attatacaat ggtcctccag   240
gtcactgtgc tggcctcaga actgaacctc aaccacactt gcaccataaa taaacccaaa   300
aggaaagaaa aacctttcaa gtttcctgag tcat                                334

<210> SEQ ID NO 21
<211> LENGTH: 73
<212> TYPE: PRT
<213> ORGANISM: Artificial Sequence
<220> FEATURE:
<223> OTHER INFORMATION: portion of the Glycophorin A including the
      transmembrane region used for fusion
```

<400> SEQUENCE: 21

Gly Glu Arg Val Gln Leu Ala His His Phe Ser Glu Pro Glu Ile Thr
1               5                   10                  15

Leu Ile Ile Phe Gly Val Met Ala Gly Val Ile Gly Thr Ile Leu Leu
                20                  25                  30

Ile Ser Tyr Gly Ile Arg Arg Leu Ile Lys Lys Ser Pro Ser Asp Val
            35                  40                  45

Lys Pro Leu Pro Ser Pro Asp Thr Asp Val Pro Leu Ser Ser Val Glu
50                  55                  60

Ile Glu Asn Pro Glu Thr Ser Asp Gln
65                  70

<210> SEQ ID NO 22
<211> LENGTH: 222
<212> TYPE: DNA
<213> ORGANISM: Artificial Sequence
<220> FEATURE:
<223> OTHER INFORMATION: portion of Glycophorin A sequence that includes
      the transmembrane region

<400> SEQUENCE: 22
ggcgagaggg tgcagctggc ccaccacttc agcgagcccg agatcaccct gatcatcttc        60
ggcgtgatgg ccggcgtgat cggcaccatc ctgctgatca gctacggcat caggaggctg       120
atcaagaaga gccccagcga cgtgaagccc ctgcccagcc ccgacaccga cgtgcccctg       180
agcagcgtgg agatcgagaa ccccgagacc agcgaccagt aa                         222

<210> SEQ ID NO 23
<211> LENGTH: 369
<212> TYPE: DNA
<213> ORGANISM: Artificial Sequence
<220> FEATURE:
<223> OTHER INFORMATION: synthetic coding sequence for an anti-idiotype
      mIgG Fd fragment - Glycophorin A fusion

<400> SEQUENCE: 23
ctcgagcacc tggcccagcc agtccatcac ctgcaatgtg gcccacccgg caagcagcac        60
caaggtggac aagaaaattg agcccagagg gcccacaatc aagccctgtc ctccatgcaa       120
atgcccagca cctggcgaga gggtgcagct ggcccaccac ttcagcgagc ccgagatcac       180
cctgatcatc ttcggcgtga tggccggcgt gatcggcacc atcctgctga tcagctacgg       240
catcaggagg ctgatcaaga agagccccag cgacgtgaag cccctgccca gccccgacac       300
cgacgtgccc ctgagcagcg tggagatcga gaaccccgag accagcgacc agtaagtgcg       360
acggccggc                                                              369

<210> SEQ ID NO 24
<211> LENGTH: 32
<212> TYPE: PRT
<213> ORGANISM: Artificial Sequence
<220> FEATURE:
<223> OTHER INFORMATION: GPI-signal attached to a DAF hydrophobic domain

<400> SEQUENCE: 24

Leu Thr Thr Ser Gly Ile Val Thr Met Ser His Gln Ala Leu Gly Phe
1               5                   10                  15

Thr Leu Thr Gly Leu Leu Gly Thr Leu Val Thr Met Gly Leu Leu Thr
                20                  25                  30

<210> SEQ ID NO 25

```
<211> LENGTH: 96
<212> TYPE: DNA
<213> ORGANISM: Artificial Sequence
<220> FEATURE:
<223> OTHER INFORMATION: Synthetic coding sequence for GPI signal - DAF
      fusion

<400> SEQUENCE: 25
ctgaccacca gcggcatcgt gaccatgagc caccaggccc tgggcttcac cctgaccggc       60
ctgctgggca ccctggtgac catgggcctg ctgacc                                 96

<210> SEQ ID NO 26
<211> LENGTH: 244
<212> TYPE: DNA
<213> ORGANISM: Artificial Sequence
<220> FEATURE:
<223> OTHER INFORMATION: synthetic sequence for anti-idiotype mIgG
      Fab-GPI-DAF fusion protein

<400> SEQUENCE: 26
ctcgagcacc tggcccagcc agagcatcac ctgcaacgtg gcccacccccg ccagcagcac      60 caaggtggac aagaagatcg agcccagggg ccccaccatc aagccctgcc cccctgcaa     120 gtgccccgcc ccctgacca ccagcggcat cgtgaccatg agccaccagg ccctgggctt     180
caccctgacc ggcctgctgg gcaccctggt gaccatgggc ctgctgacct aagtgcgacg     240
gccg                                                                  244
```